US010215995B2

(12) United States Patent
Perrault, Jr. et al.

(10) Patent No.: US 10,215,995 B2
(45) Date of Patent: Feb. 26, 2019

(54) LARGE AREA, LOW F-NUMBER OPTICAL SYSTEM

(71) Applicant: Cytonome/ST, LLC, Boston, MA (US)

(72) Inventors: Donald Francis Perrault, Jr., Brighton, MA (US); Johnathan Charles Sharpe, Hamilton (NZ)

(73) Assignee: CYTONOME/ST, LLC, Bedford, MA (US)

( * ) Notice: Subject to any disclaimer, the term of this patent is extended or adjusted under 35 U.S.C. 154(b) by 1125 days.

(21) Appl. No.: 13/896,213

(22) Filed: May 16, 2013

(65) Prior Publication Data

US 2013/0334407 A1 Dec. 19, 2013

Related U.S. Application Data

(60) Provisional application No. 61/647,821, filed on May 16, 2012.

(51) Int. Cl.
| | | |
|---|---|---|
| *G02B 27/30* | (2006.01) | |
| *G01N 21/64* | (2006.01) | |
| *G01N 21/53* | (2006.01) | |
| *B01L 3/00* | (2006.01) | |
| *G01N 15/14* | (2006.01) | |
| *G01N 21/05* | (2006.01) | |

(52) U.S. Cl.
CPC ........ *G02B 27/30* (2013.01); *B01L 3/502715* (2013.01); *G01N 15/1484* (2013.01); *G01N 21/53* (2013.01); *G01N 21/64* (2013.01); *G01N 21/645* (2013.01); *B01L 2300/0654* (2013.01); *B01L 2300/0816* (2013.01); *G01N 21/05* (2013.01); *G01N 2021/6484* (2013.01)

(58) Field of Classification Search
CPC .... G01N 21/64; G01N 21/53; G01N 15/1484; G01N 21/05; G01N 2021/6484; G01N 2021/6482; G01N 2021/6486; G01N 2021/0346; G01N 21/648; G01N 21/645; G01N 2021/0357; B01L 2300/0654; B01L 2300/0816; B01L 3/5027; B01L 3/502715
USPC ............... 250/573–576, 222.2, 458.1, 483.1; 356/301, 336, 337, 344
See application file for complete search history.

(56) References Cited

U.S. PATENT DOCUMENTS

| | | | |
|---|---|---|---|
| 3,741,621 A | 6/1973 | McCrobie | |
| 4,127,773 A * | 11/1978 | West | B07C 5/3427 250/226 |
| 4,348,081 A | 9/1982 | Betensky | |
| 4,900,139 A | 2/1990 | Kreitzer | |
| 5,022,724 A * | 6/1991 | Shechterman | G02B 13/14 359/354 |

(Continued)

*Primary Examiner* — Georgia Y Epps
*Assistant Examiner* — Don Williams
(74) *Attorney, Agent, or Firm* — McCarter & English, LLP; David R. Burns

(57) ABSTRACT

Large area, low f-number optical systems, and microfluidic systems incorporating such optical systems, are disclosed. Large area, low f-number optical systems may be used to collect light from plurality of micro channels associated with a plurality of flow cytometers. The optical systems may be configured to collect light from a source area having an object lateral length or width within a range of 25 mm and 75 mm, configured to have an f-number within a range of 0.9 to 1.2, and configured to have a working distance within a range of 10 mm to 30 mm.

25 Claims, 25 Drawing Sheets

(56) References Cited

U.S. PATENT DOCUMENTS

| | | | |
|---|---|---|---|
| 5,455,713 A | 10/1995 | Kreitzer | |
| 5,808,804 A | 9/1998 | Moskovich | |
| 6,297,061 B1 * | 10/2001 | Wu | G01N 33/5005 210/198.2 |
| 6,510,007 B1 | 1/2003 | Blasenheim | |
| 6,608,572 B1 * | 8/2003 | Venkitachalam | H03H 17/0614 341/143 |
| 6,808,075 B2 | 10/2004 | Bohm et al. | |
| 6,976,590 B2 | 12/2005 | Deshpande et al. | |
| 7,110,192 B2 | 9/2006 | Sauter et al. | |
| 7,179,423 B2 | 2/2007 | Bohm et al. | |
| 7,211,442 B2 | 5/2007 | Gilbert et al. | |
| 7,492,522 B2 | 2/2009 | Gilbert et al. | |
| 8,961,764 B2 * | 2/2015 | Trost | G01N 21/645 204/452 |
| 2002/0097506 A1 | 7/2002 | Schauss | |
| 2002/0197733 A1 | 12/2002 | Bohm et al. | |
| 2003/0015425 A1 | 1/2003 | Bohm et al. | |
| 2003/0128910 A1 * | 7/2003 | Naghieh | G01N 21/6452 385/15 |
| 2004/0256541 A1 * | 12/2004 | Cofer et al. | 250/221 |
| 2006/0233668 A1 * | 10/2006 | Resch-Genger | B01L 3/5027 422/82.08 |
| 2008/0213821 A1 * | 9/2008 | Liu et al. | 435/39 |
| 2010/0110423 A1 * | 5/2010 | Villaumie | G01J 3/02 356/301 |
| 2011/0036992 A1 * | 2/2011 | Fukumoto | B01L 3/502715 250/458.1 |

* cited by examiner

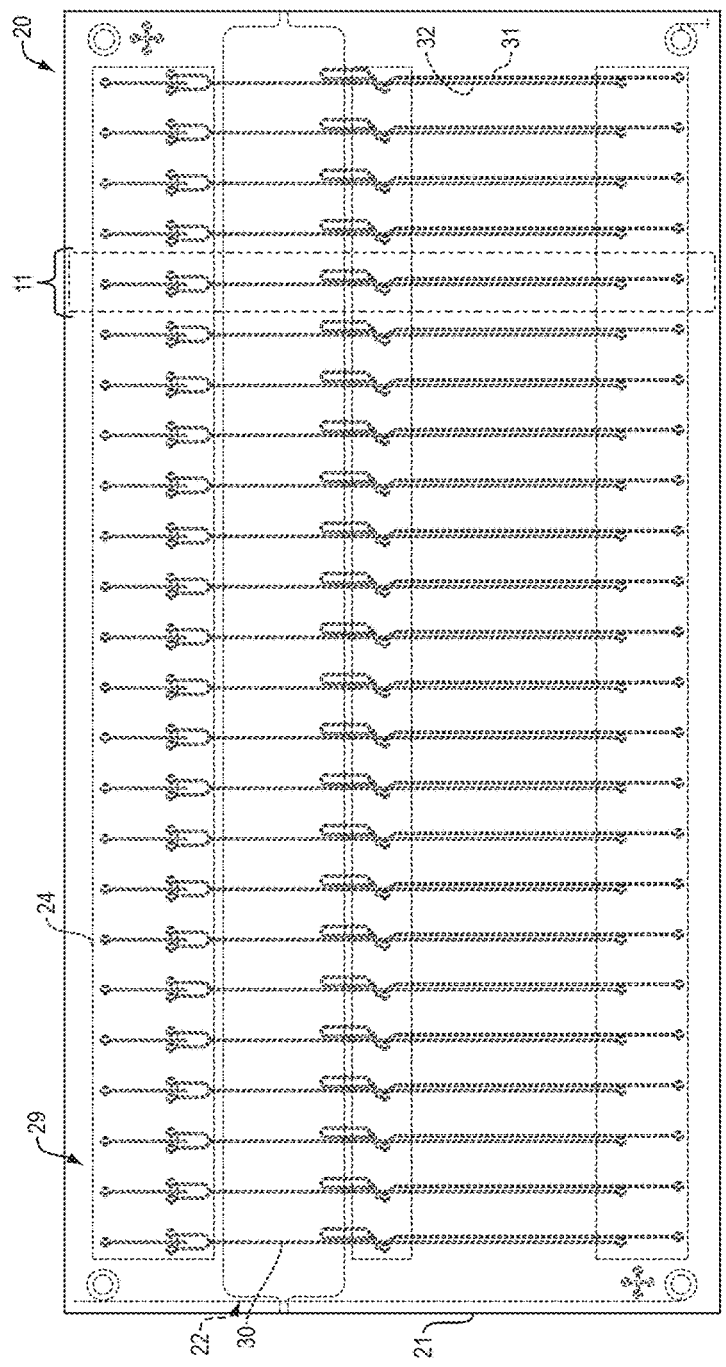
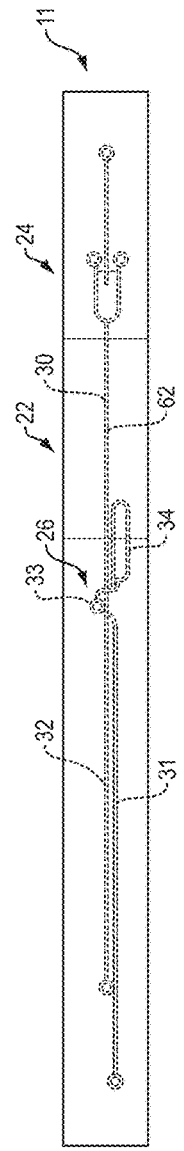
FIG. 2
FIG. 3

LARGE AREA, LOW F-NUMBER OPTICAL SYSTEM

RELATED APPLICATION

The present application claims benefit of, and priority to, U.S. Provisional Patent Application No. 61/647,821, filed May 16, 2012, which is herein incorporated by reference in its entirety.

BACKGROUND

In a system, such as a microfluidic system, that conveys particles through one or more channels, an optical system may be used for monitoring, analyzing or detecting the particles. Optical systems may be useful, for example in particle sorting systems, which sort a stream of particles flowing through one or more channels based on a predetermined characteristic.

SUMMARY

Embodiments include a large area, low f-number optical system, an optical system for collecting and collimating light from a plurality of micro channels associated with a plurality of flow cytometers, and a multi-channel microfluidic system including such optical systems.

An embodiment includes a large area, low f-number optical system for collecting and collimating light from a plurality of micro channels associated with a plurality of flow cytometers. The optical system includes a plurality of optical elements disposed along an optical path of the system, and a mounting system for mounting the plurality of optical elements along the optical path. The optical system is configured to collect light from the plurality of micro channels distributed over a source area having a length or width within a range of about 10 mm to about 75 mm, and to have a working distance between the source area and a first optical element in the plurality of optical elements along the optical path within a range of about 10 mm to about 30 mm.

In some embodiments, the optical system is further configured to have a maximum distortion within a range of about 0.005% to about 0.05% for light from all points in the source area. In some embodiments, the optical system is further configured to have an f-number within a range of about 0.9 to about 1.2 for light from all points in the source area.

In some embodiments, the plurality of optical elements includes a plurality of non-aspheric lenses. In some embodiments, the optical system is telecentric. The optical system may have about one to one magnification. The magnification tolerances of the optical system may be within a range of about 0.9995 to about 1.0005. The magnification of the optical system may be within a range of about 0.5 to 5.

In some embodiments, the optical system is configured such that at least 65% of the energy incident on an image plane emitted by point source in the source area is encircled by a 200 micron diameter circle at the image plane for all points in the source area. The optical system may be configured such that at least 65% of the energy incident on an image plane within a wavelength range of about 540 nm to about 820 nm emitted by a point source in the source area is encircled by a 200 micron diameter circle for all points in the source area. The optical system may be configured such that at least 75% of the energy incident on an image plane within a wavelength range of about 665 nm to about 820 nm emitted by a point source in the source area is encircled by a 200 micron diameter circle for all points in the source area.

In some embodiments, a first optical element in the plurality of optical elements disposed along the optical path includes a first lens having a concave surface facing the source area. In some embodiments, the plurality of optical elements includes seven or more substantially co-axial lenses that collect and collimate the light. The plurality of optical elements may include nine or more substantially co-axial lenses that collect and collimate the light. The plurality of optical elements may include fourteen or more substantially co-axial lenses. The plurality of optical elements may include eighteen or more substantially co-axial lenses.

In some embodiments, the plurality of optical elements includes an optical filter disposed in the optical path. In some embodiments, the plurality of optical elements includes a grating.

In some embodiments, the optical system has a longitudinal chromatic aberration within a range of about −0.350 mm to about 0.350 mm. In some embodiments, the plurality of optical elements includes a plurality of lenses. Each lens in the plurality of lenses may include an optical material having an autofluorescence within a range of about 20×-2× less than that of BK7 glass.

In some embodiments, the optical system has a transmission within a range of 70% to 99% over a wavelength range of about 350 nm to about 900 nm. In some embodiments, an output relative illumination of the optical system is within a range of about 70% to about 95% for all points in the source area. In some embodiments, the optical system has a resolution within a range of about 20 um to about 260 um. In some embodiments, the optical system has a depth of field within a range of about −250 μm to about 250 μm.

In some embodiments, the optical system also includes an array of input apertures disposed in proximity to the source area. The optical system may also include an array of output apertures disposed in proximity to an image plane. In some embodiments, the optical system also includes an array of apertures positioned to filter in the Fourier transform plane.

In some embodiments, a diameter of each output aperture in the array of output apertures increases with increasing lateral distance between the output aperture and a center of the optical path. A diameter of each output aperture in the array of output apertures may be proportional to a selected encircled energy diameter for a corresponding position in the image plane.

In some embodiments, the plurality of optical elements includes a first set of optical elements that collects and collimates light and a second set of optical elements that focuses the collimated light. A last optical element along the optical path in the second set of optical elements may be a lens with a concave surface facing an imaging plane. A distance between a first optical element in the first set of optical elements along the optical path and a last optical element in the second set of optical elements along the optical path may be within a range of about 500 mm to about 800 mm. In some embodiments, the first set of optical elements includes a first set of lenses, and the second set of optical elements includes a second set of lenses. The first set of lenses and the second set of lenses may form an air-spaced achromat lens pair. A last lens along the optical path in the first set of lenses may have a diameter within a range of about 65 mm to about 70 mm, and a first lens along the optical path in the second set of lenses may have a diameter within a range of about 65 mm to about 70 mm. In some embodiments, the first set of lenses includes seven or more substantially co-axial lenses and the second set of lenses includes seven or more substantially co-axial lenses. The first set of lenses may include nine or more substantially co-axial lenses and the second set of lenses may include nine or more substantially co-axial lenses.

In some embodiments, the plurality of flow cytometers is associated with a multi-channel sorter.

Another embodiment includes a large area, low f-number optical system including a plurality of optical elements disposed along an optical path of the system, and a mounting system for mounting the plurality of optical elements along the optical path. The optical system is configured to collect light from a source area having an object lateral length or width within a range of about 25 mm to about 75 mm and have an f-number within a range of about 0.9 to about 1.2 for light from all points in the source area. The optical system is also configured to have a working distance between the source area and a first optical element in the plurality of optical elements closest to the source area within a range of about 10 mm to about 30 mm, and have a maximum distortion within a range of about 0.005% to about 0.05% for light from all points in the source area.

In some embodiments, the optical system has a depth of field within a range of about −250 µm to about 250 µm.

In some embodiments, the optical system is configured for collecting light from a plurality of micro channels. The micro channels may be associated with a multi-channel sorting system. The micro channels may be associated with a plurality of flow cytometers.

In some embodiments, the optical system is configured for simultaneously collecting fluorescent light emitted by a plurality of particles flowing in a plurality of micro channels.

An embodiment includes an optical system having a plurality of optical elements disposed along an optical path of the system The plurality of optical elements includes a first set of lenses configured to collect and collimate light from a source area and a second set of lenses disposed along the optical path after the first set of lenses and configured to focus light. The first set of lenses includes: a first meniscus lens in the optical path having a concave surface facing the source area; a first plurality of intermediate lenses positioned in the optical path after the first meniscus lens; and a first biconvex lens positioned in the optical path after the first plurality of intermediate lenses. The second set of lenses includes: a second biconvex lens positioned in the optical path; a second plurality of intermediate lenses positioned in the optical path after the second biconvex lens; and a second meniscus lens positioned in the optical path after the second plurality of intermediate lenses and having a concave surface facing an image plane. The optical system also includes a mounting system for mounting the plurality of lenses along the optical path.

In some embodiments, the first plurality of intermediate lenses includes a lens having a concave surface facing the first meniscus lens and the second plurality of intermediate lenses includes a lens having a concave surface facing the second meniscus lens. In some embodiments, the first plurality of intermediate lenses includes 5 or more lenses and the second plurality of intermediate lenses includes 5 or more lenses. The first plurality of intermediate lenses may include seven or more lenses and the second plurality of intermediate lenses may include seven or more lenses.

In some embodiments, the first biconvex lens and the second biconvex lens each have a diameter within the range of about 50 mm to about 200 mm.

In some embodiments, the optical system is configured to collect light from a source area having an object lateral length or width within a range of about 25 mm to about 75 mm. In some embodiments, the optical system is configured to have an f-number within a range of about 0.9 to about 1.2 for light collected from all points in the source area. In some embodiments, the optical system is configured to have a working distance between the source area and the first meniscus lens within a range of about 10 mm to about 30 mm. In some embodiments, first set of lenses and the second set of lenses form an asymmetrical lens system pair having about one to one imaging.

Another embodiment includes a multi-channel microfluidic system with a receptacle for receiving a multi-channel microfluidic chip having a plurality of microfluidic channels and one or more light sources for illuminating at least a portion of each micro-fluidic channel in the plurality of microfluidic channels. The multi-channel microfluidic system includes an optical system in accordance with various embodiments. The multi-channel microfluidic system also includes one or more detectors for detecting light output from the optical system.

The microfluidic channels may be associated with a plurality of flow cytometers. The microfluidic system may be a particle sorting system that sorts particles in the plurality of microfluidic channels.

In some embodiments, the multi-channel microfluidic system also includes a plurality of optical fibers for receiving light from the optical system and transmitting the light to the one or more detectors. Each optical fiber may receive light from one microfluidic channel. The one or more light sources may simultaneously illuminate at least a portion of each micro-fluidic channel.

In some embodiments, the optical system includes a long pass filter having an optical density profile selected to attenuate a magnitude of an incident scattered light signal from at least one of the one or more light sources to be comparable to a magnitude of an expected incident fluorescent signal.

An embodiment includes a method of detecting fluorescence and light scatter from a liquid and/or a particle in a channel of a microfluidic chip. The method includes illuminating the channel with a light source. The method also includes receiving illumination source light scattered by the liquid and/or particle and fluorescent light emitted from the liquid and/or particle using an optical system having a primary optical path and a long pass filter in the primary optical path. The method includes attenuating the scattered source light using the long pass filter such that a magnitude of the attenuated scattered source light is comparable to a magnitude of the emitted fluorescent light in the primary optical path after the long pass filter. The method also includes detecting the attenuated scattered source light and the emitted fluorescent light using one or more detectors in the primary optical path.

BRIEF DESCRIPTION OF THE FIGURES

The following is a brief description of the drawings, which are presented for the purposes of illustrating the disclosure set forth herein and not for the purposes of limiting the same. A more complete understanding of the components, processes, and apparatuses disclosed herein can be obtained by reference to the accompanying figures. These figures are intended to demonstrate the present disclosure and are not intended to show relative sizes and dimensions or to limit the scope of the disclosed embodiments. Further, like reference numbers refer to like elements throughout.

FIG. 2 is a bottom view of the microfluidic device of FIG. 1.

FIG. 3 is a detail view of FIG. 2 showing a single sorter.

DETAILED DESCRIPTION

Figure 1:
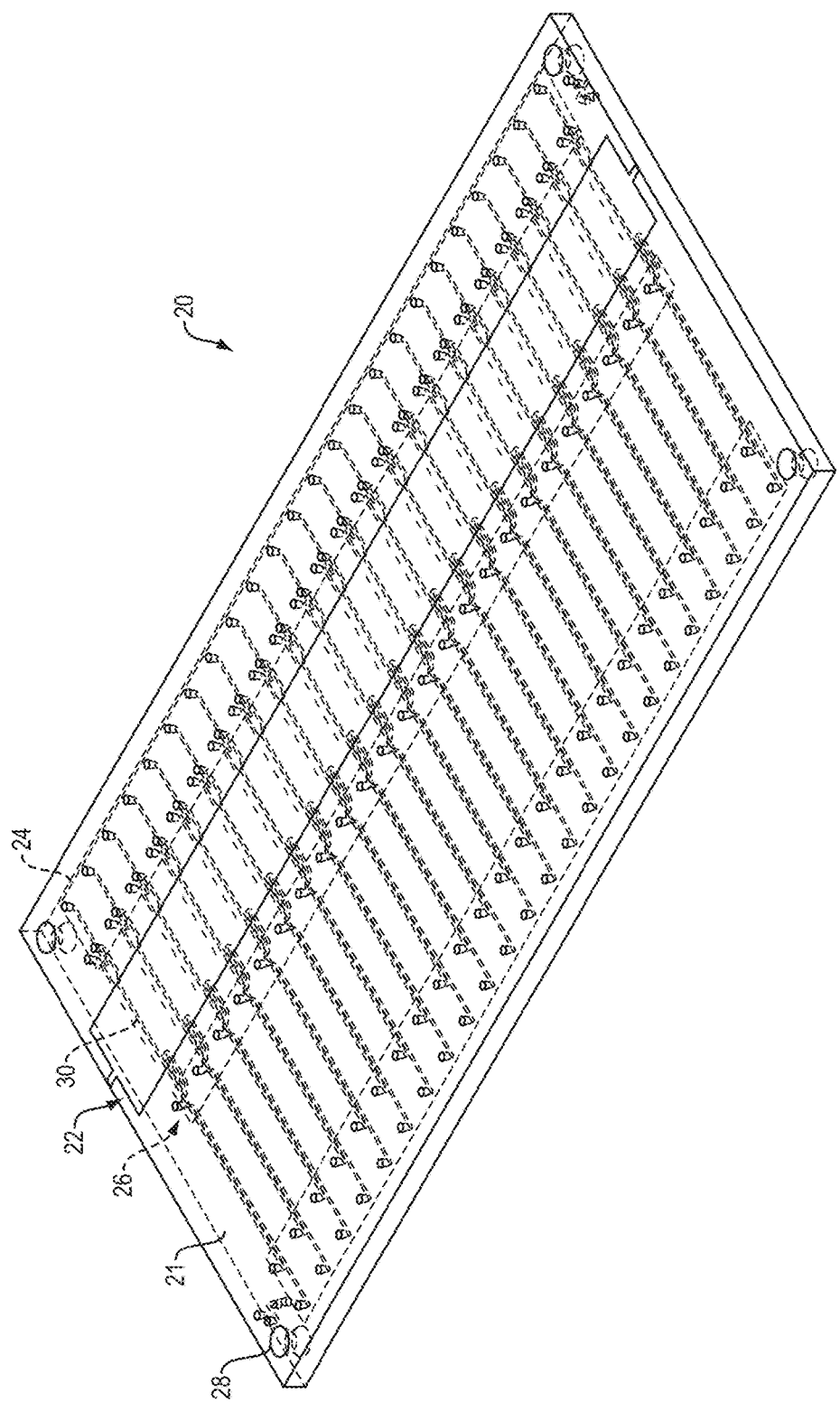
FIG. 1 is a perspective view of a microfluidic device with which an exemplary optical system may be employed, in accordance some embodiments.

Embodiments of provide a large area, low f-number optical system for collecting and collimating light from a plurality of micro channels associated with a plurality of flow cytometers, and a multi-channel microfluidic system including the optical system. The present invention is described below relative to illustrative embodiments. Those skilled in the art will appreciate that the present invention may be implemented in a number of different applications and embodiments and is not specifically limited in its application to the particular embodiments depicted herein.

The inventors found that currently available optical systems could not meet the demands of new multi-channel flow cytometry systems developed by the inventors, in which light from multiple particles (e.g., cells) flowing in multiple microfluidic channels distributed over a source area is collected for measurement and detection by a single optical system. For example, shortcomings of various currently available optical systems included: too high an f-number, too short a working distance, too small an object imaging area, insufficient resolution, too much chromatic or spherical aberration, insufficient image flatness, excess autofluorescence from optical elements, insufficient depth of field, insufficient field of view, insufficient transmission of light across the field of view, high cost of aspherical lenses, etc. Some embodiments include optical systems that address one or more of the aforementioned shortcomings.

Some embodiments include a large area, low f-number optical system configured to collect light from a source area having an object lateral length or width within a range of about 25 mm and about 75 mm, configured to have an f-number within a range of about 0.9 to about 1.2, and configured to have a working distance within a range of about 10 mm to 30 mm. The optical system may have a combination of optical features particularly well suited to the detection of particles (e.g., cells) simultaneously and/or asynchronously flowing in multiple micro channels.

Some embodiments include a large area, low f-number optical system for collecting and collimating light from a plurality of micro channels associated with a plurality of flow cytometers. The optical system may be configured to collect light from the plurality of micro channels distributed over a source area. The optical system may be configured to have an f-number within a range of about 0.9 to about 1.2 for all points in the source area. The optical system may further be configured to have a working distance of between about 10 mm to about 30 mm.

Some embodiments include a multi-channel microfluidic system that includes a large area, low f-number optical system. The optical system may include a receptacle for receiving a multi-channel microfluidic chip having a plurality of microfluidic channels, and a light source for simultaneously illuminating at least a portion of each micro-fluidic channel in the plurality of microfluidic channels. The microfluidic system may further include a low f-number optical system for receiving and filtering light emitting from the plurality of microfluidic channels and one or more detectors for detecting light output from the optical system.

FIGS. 1 and 2 illustrate a microfluidic device in the form of a microfluidic chip 20 that may be used in conjunction with exemplary embodiments. The microfluidic chip has channels 30 (e.g., micro channels) distributed over a source area 22 that are associated with a plurality of flow cytometers 11. FIG. 3 depicts a single flow cytometer 11 of the chip. The channels 30 may be suitable for conveying a substance, such as particles or cells, therethrough. The channels 30 may be micro channels. The microfluidic chip 20 includes a substrate 21 in which the channels 30 are disposed. The channels transport fluid and/or particles through the microfluidic chip 20 for processing, handling, and/or performing any suitable operation on a liquid sample (e.g., a particle sorting system). As used herein, the term particles includes, but is not limited to, cells (e.g., blood platelets, white blood cells, tumorous cells, embryonic cells, spermatozoa, etc.), synthetic beads (e.g., polystyrene), organelles, and multi-cellular organisms. Particles may include liposomes, proteoliposomes, yeast, bacteria, viruses, pollens, algae, or the like. Particles may also refer to non-biological particles. For example, particles may include metals, minerals, polymeric substances, glasses, ceramics, composites, or the like. Additionally, particles may include cells or beads with fluorochrome conjugated antibodies.

As used herein, the term "microfluidic" refers to a system or device for handling, processing, ejecting and/or analyzing a fluid sample including at least one channel having microscale dimensions. The term "channel" as used herein refers to a pathway formed in or through a medium that allows for movement of fluids, such as liquids and gases. The term "microchannel" refers to a channel, preferably formed in a microfluidic system or device, having cross-sectional dimensions in the range between about 1.0 µm and about 500 µm, preferably between about 25 µm and about 350 µm, and most preferably between about 50 µm and about 300 µm. One of ordinary skill in the art will be able to determine an appropriate volume and length of the channel for the desired application. The ranges above are intended to include the above-recited values as upper or lower limits. The channel can have any selected cross-sectional shape or arrangement, non-limiting examples of which include a linear or non-linear configuration, a U-shaped or D-shaped configuration, and/or a rectangular, triangular, elliptical/oval, circular, square, or trapezoidal geometry. A microfluidic device or chip may include any suitable number of channels for transporting fluids. The microfluidic chip may include a disposable cartridge with a closed channel system of capillary size.

The microfluidic chip may be any device or chip including channels for flowing a substance, such as particles (e.g., cells) therethrough. For example, the microfluidic chip may include a particle sorting system, such as the particle sorting systems described in U.S. patent application Ser. No. 10/179,488, which issued as U.S. Pat. No. 6,808,075, and U.S. patent application Ser. No. 10/329,008, which issued as U.S. Pat. No. 6,976,590, the contents of both patent applications are herein incorporated by reference in their entirety. Other suitable microfluidic systems are described in U.S. patent application Ser. No. 10/028,852, which issued as U.S. Pat. No. 7,179,423, U.S. patent application Ser. No. 10/027,484, which published as U.S. Patent Publication No. 2003-0015425 A1, U.S. patent application Ser. No. 10/027,516, which published as U.S. Patent Publication No. 2002-0197733 A1, and U.S. patent application Ser. No. 10/607,287, which issued as U.S. Pat. No. 7,211,442, all of which are herein incorporated by reference in their entirety.

A microfluidic particle (e.g., cell) sorting system for a microfluidic chip, in accordance some embodiments, may have a wide variety of applications as a therapeutic medical device enabling cell-based therapies, such as blood transfusion, bone marrow transplants, and/or mobilized peripheral blood implants. Embodiments of microfluidic sorting systems may be capable of selecting cells based on intrinsic characteristics as determined by interaction of light with the cells (e.g., scatter, reflection, and/or auto fluorescence) independent of protocols and necessary reagents. A microfluidic system may employ a closed, sterile, disposable cartridge including a microfluidic chip. The microfluidic system may process particles (e.g., cells) at high speeds, and deliver particles (e.g., cells) with high yield and high purity.

In the embodiment of FIGS. 1 and 2, the microfluidic chip 20 includes an input region 24 in which fluid, and particles (e.g., cells) are input into the microfluidic chip 20. As shown in FIG. 1, fluid and particles may be input through a first side 28 of the microfluidic chip. Particles in channels 30 are detected while flowing through the source area 22, which may be described as a measurement region. At the source area 22, individual particles 62 (see FIG. 3) may be inspected or measured for a particular characteristic, such as size, form, fluorescence intensity, etc. Source area 22 may be illuminated through a second side 29 of the microfluidic chip (see FIG. 2). Although microfluidic chip 20 includes twenty-four channels 30 flowing through the source area 22, one of ordinary skill in the art will appreciate that microfluidic chip 20 may include more channels or fewer channels flowing through the source area (e.g., such as 2, 4, 8, 24, 36, 72, 144, or 288 channels).

As noted above, a microfluidic chip for use with some embodiments may be a sorter. For example, in microfluidic chip 20, some of the particles flowing in each channel 30 are selectively directed into downstream channels 31 in a sorting region 26 as opposed to downstream channels 32. The sorting may be accomplished through one or more mechanisms, which may include but are not limited to: mechanical displacement of the particle by deflecting a membrane with a piezo actuator, optical force techniques, dielectric methods, and other suitable sort techniques. For example, in some embodiments a microfluidic chip 20 includes bubble valves for selectively directing particles into micro channels 31.

Details of a sorting channel system 11 for a single channel including bubble valves are provided below with respect to FIG. 4.

As illustrated by FIGS. 1 and 2, the microfluidic chip 20 may include a plurality of sorting channels systems 11 operating in series and/or in parallel on the chip substrate 21. For example, microfluidic chip 20 includes twenty-four parallel sorting channel systems 11 that perform sorting in sorting region 26.

A microfluidic chip 20 for use with some embodiments may incorporate multiple sorting regions in series. For example, in some embodiments a microfluidic chip includes a second sorting region downstream from the first sorting region. In some embodiments, the second sorting region provides additional sorting based on a predetermined characteristic to increase purity, or provides sorting of particles based on a different predetermined characteristic. In embodiments with a second sorting region, an enrichment region may be provided between the first sorting region and the second sorting region to adjust selected parameters within the fluid containing the particles to be sorted. For example, the enrichment region may remove excess sheath fluid from collected particles after a first sorting process before performing a secondary sorting process.

When performing parallel sorting, the microfluidic chip 20 may pass non-selected particles from each sorting channel out of the chip for collection and/or disposal. In some embodiments, the non-selected particles are summed into a single summing channel. In some embodiments, the non-selected particles are not summed into a single summing channel. For example, microfluidic chip 20 separately passes the non-selected particles from each sorting channel 32 to a collector or disposal device located off-chip. An advantage is derived from using a plurality of summing channels for non-selected particles, and/or zero summing channels for the non-selected particles, in that the potential for clogging may be reduced. By reducing the potential for clogging, the efficiency and lifetime of the sorting system may be increased. The microfluidic chip may utilize one or more summing channels for the selected particles from the array of sorting channels for collection of all of the selected particles or for subsequent secondary sorting of the selected particles.

In addition, a system that employs the microfluidic chip, or the microfluidic chip itself, may include a sensor for measuring the velocity of one or more particles in a sorting channel to facilitate more accurate sorting. The ability to measure the velocity of particles within the parallel channels allows for the sorting system to have channels of different lengths and spacings while maintaining accurate sorting, and/or to account for variations in particle velocities due to other conditions.

In some embodiments, spacing between a plurality of parallel sorting channels in a particle sorting system may be varied in different regions to conserve resources. For example, in a detection region of a chip substrate, parallel sorting channels may be spaced closer together than in a sorting region of a chip substrate.

Figure 4:
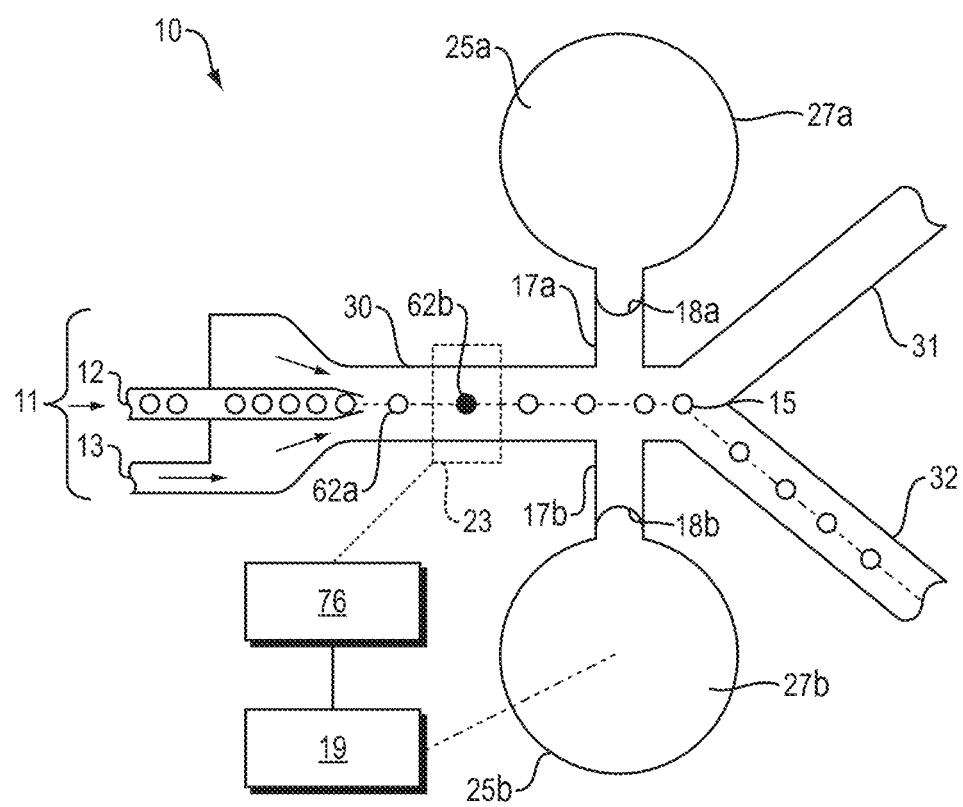
FIG. 4 schematically depicts a sorting channel system of the microfluidic device of FIG. 1.

FIG. 4 schematically illustrates the sorting functionality associated with a sorting channel system 11 of microfluidic chip 20. Microfluidic chip 20 has a first supply duct 12 for introducing a stream of particles 62 and a second supply duct 13 for supplying a carrier liquid. The first supply duct 12 forms a nozzle 12a, and a stream of particles 62 is introduced into the flow of carrier liquid. The first supply duct 12 and the second supply duct 13 connect with the channel 30, which may also be referred to as a measurement duct, that conveys the particles $62a$, $62b$ suspended in the carrier liquid. The channel 30 branches into a first branch 31 and a second branch 32 at a branch point 15. A measurement region 23 is defined in the channel 30 and is associated with a detection and measurement system 76 to sense a predetermined characteristic of particles in the measurement region 23. The measurement region 23 corresponds to the source area 22 of the microfluidic chip (see also FIGS. 1 and 2). Two opposed bubble valves $27a$ and $27b$ are positioned in communication with the channel 30 and are spaced opposite each other. The bubble valves $27a$, $27b$ communicate with channel 30 through a pair of opposed side passages $17a$ and $17b$, respectively. Liquid is allowed to partly fill these side passages $17a$ and $17b$ to form a meniscus $18a$, $18b$ in each. For each side passage $17a$, $17b$, the corresponding meniscus $18a$, $18b$ defines an interface between the carrier liquid and a gas in the reservoir of the associated bubble valve $27a$, $27b$. An external actuator 19 is also provided for actuating the first bubble valve $28a$, which momentarily causes a flow disturbance in the channel 30 to deflect the flow therein when activated by the actuator 19. The second bubble valve $27b$ serves as a buffer for absorbing the pressure pulse created by the first bubble valve $27a$.

The first side passage $17a$ is hydraulically connected to a compression chamber $25a$ in the first bubble valve $27a$, so that if the pressure in compression chamber $25a$ is increased, the flow in channel 30 near the side passage is displaced away from first side passage $17a$, substantially perpendicular to the normal flow in the duct. The second side passage $17b$, positioned opposite of the first side passage $17a$ is hydraulically connected to a buffer chamber $25b$ in the second bubble valve $27b$ for absorbing pressure transients. This second side passage $17b$ co-operates with the first side passage $17a$ to direct the before-mentioned liquid displacement caused by pressurizing the compression chamber $25a$, so that the displacement has a component perpendicular to the normal flow of the particles $62a$, $62b$ through the channel 30.

Upon pressurizing the compression chamber $25a$, an amount of liquid is transiently discharged from the first side passage $17a$. Due to the resiliency of the second side passage $17b$, the pressurized discharge results in a transient flow of the liquid in the channel 30 into the second side passage $17b$. The co-operation of the two side passages $17a$, $17b$ and the fluidic structures they interconnect (bubble valves $27a$, $27b$) causes the flow through the channel 30 to be transiently moved sideways back and forth upon pressurizing and depressurizing of the compression chamber $25a$ induced by the external actuator 19 in response to the signal raised by the measurement and detection system 76. This transient liquid displacement, having a component perpendicular to the normal flow in the channel 30, can be applied in deflecting particles having predetermined characteristics $62b$ to separate them from the remaining particles $62a$ in the mixture.

As shown, the channel 30 branches at the branch point 15 into two branches 31, 32 and the flow rates in these branches are adjusted so that the particles normally stream through the second of the two branches 32. The angle between the branches 31, 32 is between 0 and 180 degrees, preferably between 10 and 45 degrees. However, the angle can even be 0 degrees, which corresponds to two parallel ducts with a straight separation wall between them.

In a suspension introduced by the first supply duct 12, two types of particles can be distinguished: normal particles $62a$ and particles of interest $62b$. Upon sensing the predetermined characteristic in a particle $62b$ in the measurement region 23, the detection and measurement system 76 sends a signal to the external actuator 19. When signaled by the detection and measurement system 76, the external actuator 19 activates the first actuator bubble valve 27a to create a flow disturbance in the channel 30 between the side passages 17a, 17b. The flow disturbance deflects the particle 62b having the predetermined characteristic so that it flows down the first branch duct 31 rather than the second branch duct 32. The detection and measurement system 76 communicates with the actuator 19, so that when the detection and measurement system 76 senses a predetermined characteristic in a particle, the actuator activates the first bubble valve 27a to cause pressure variations in the reservoir 25a of the first bubble valve. Conversely, when operating in other sorting modes such as when performing particle enrichment, the sort mechanism may be used to deflect unwanted particles. The activation of the first bubble valve 27a deflects the meniscus 18a in the first bubble valve 27a and causes a transient pressure variation in the first side passage 17a. The second side passage 17b and the second bubble valve 27b absorb the transient pressure variations in the channel 30 induced via the actuator 19. Basically, the reservoir 25b of the second bubble valve 27b is a buffer chamber having a resilient wall or containing a compressible fluid, such as a gas. The resilient properties allow the flow of liquid from the measurement duct 14 into the second side passage 24b, allowing the pressure pulse to be absorbed and preventing disturbance to the flow of the non-selected particles in the stream of particles. For simplicity, in FIG. 4 the compression chamber is depicted as first bubble valve 27a and the buffer chamber is depicted as second bubble valve 27b; however, other designs and configurations may be employed for the compression chamber and for the buffer chamber. For example, FIG. 3 shows a sorter 11 including a compression chamber 33 opposite a buffer chamber 34 having an elongated structure.

Figure 5:
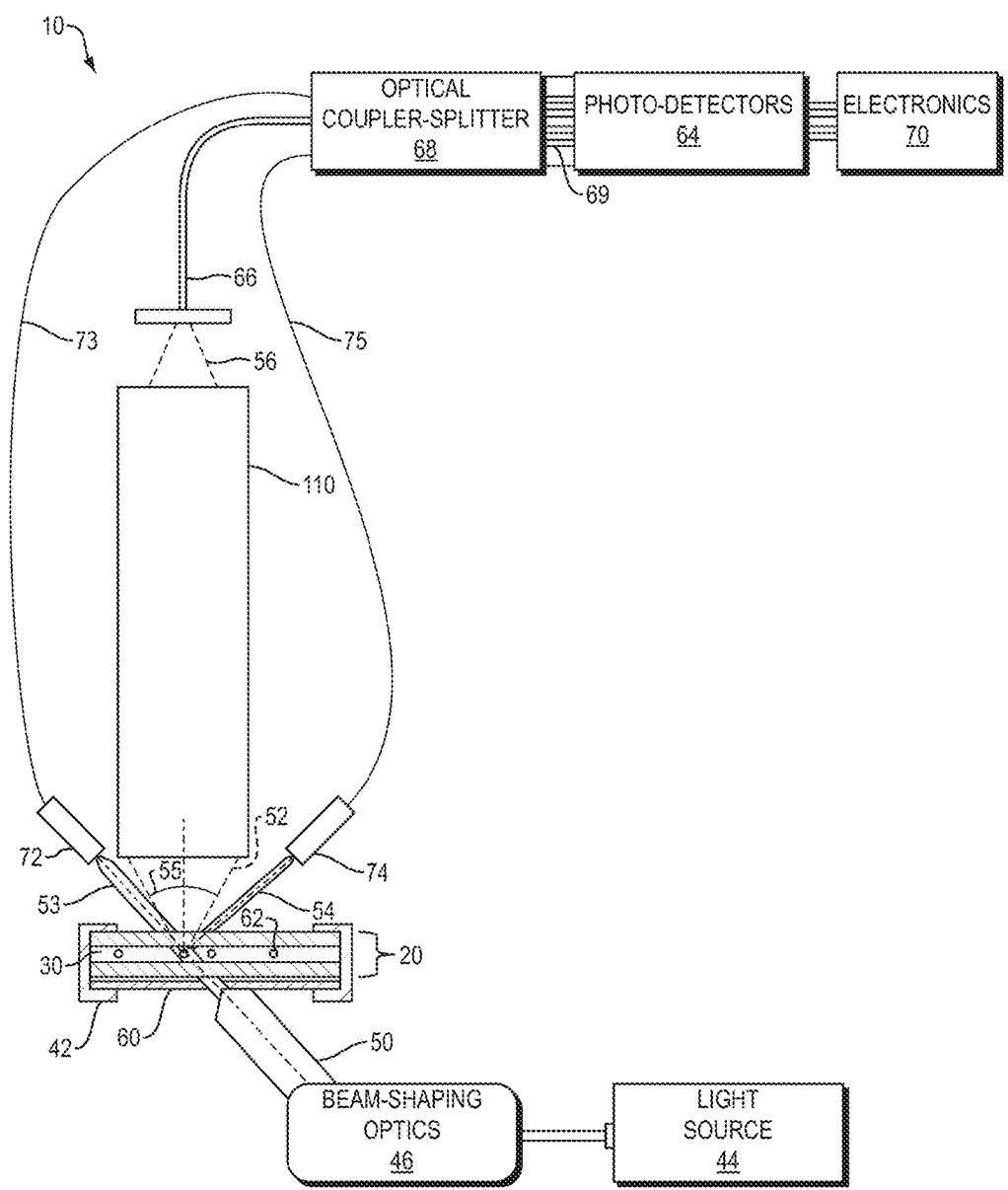
FIG. 5 schematically depicts a microfluidic system including an optical system for collecting light from micro channels of the microfluidic device depicted in FIG. 1, in accordance with some embodiments.
Figure 6:
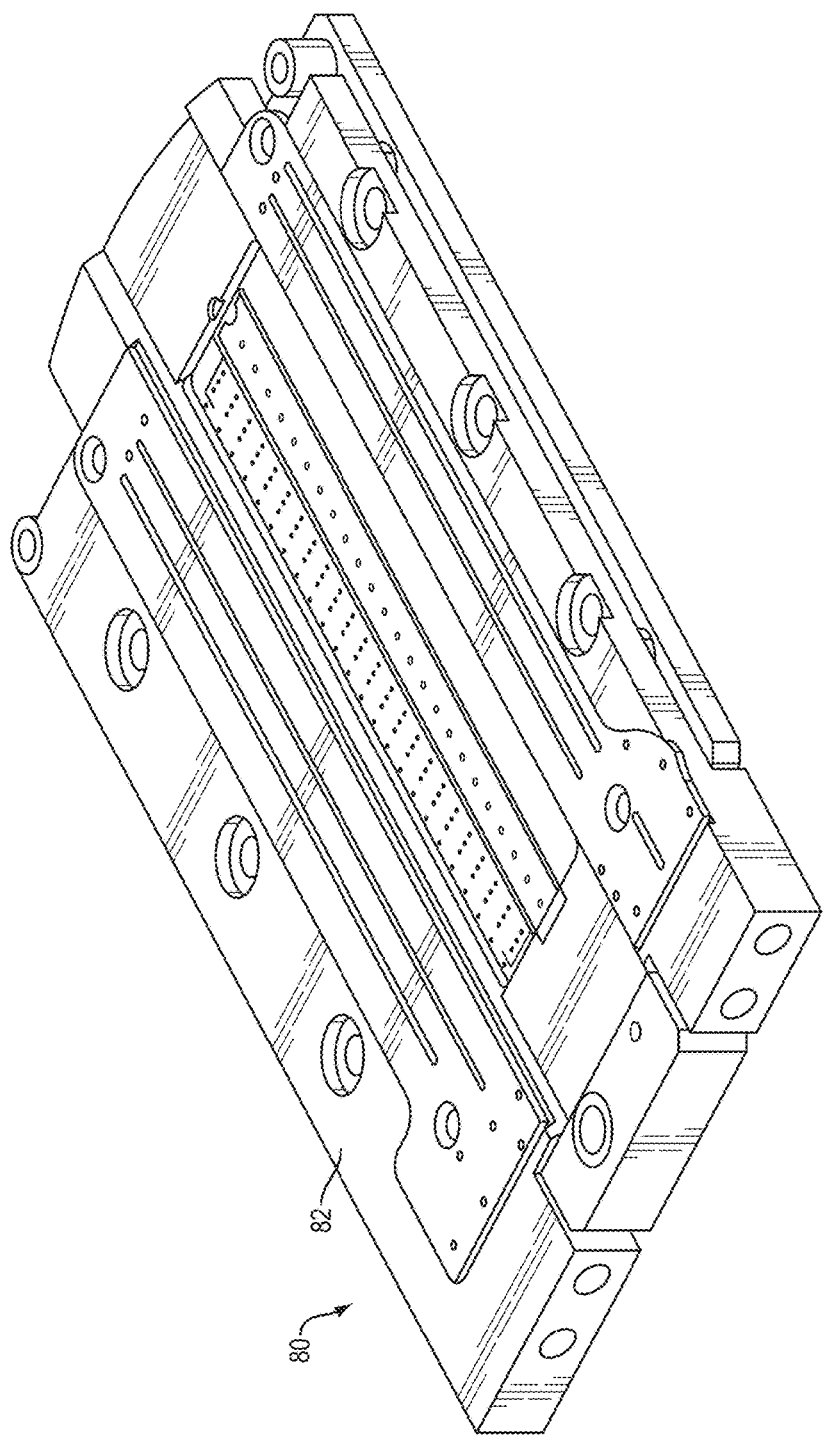
FIG. 6 is a perspective view of a chip holder and a microfluidic device, in accordance with some embodiments.
Figure 8:
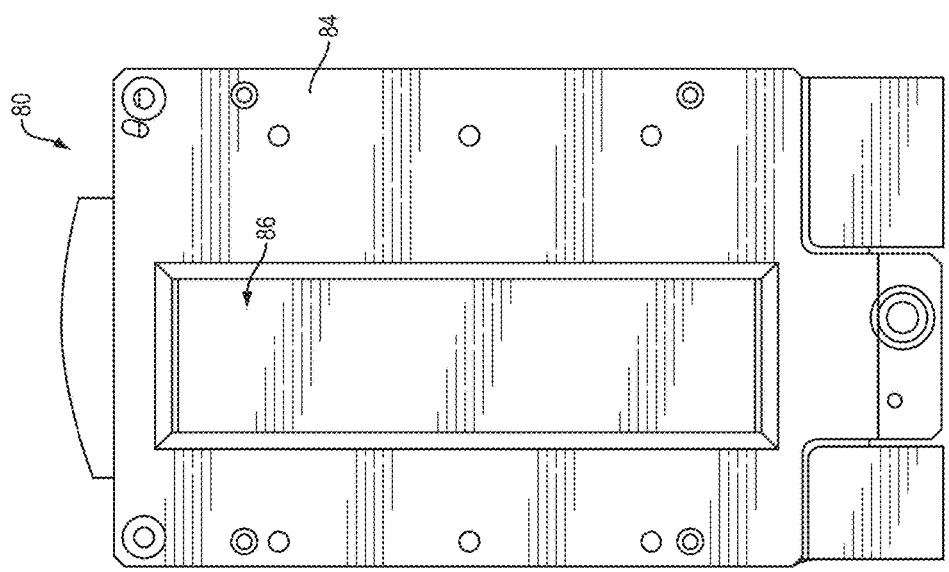
FIG. 8 is a bottom view of the chip holder of FIG. 6.
Figure 7:
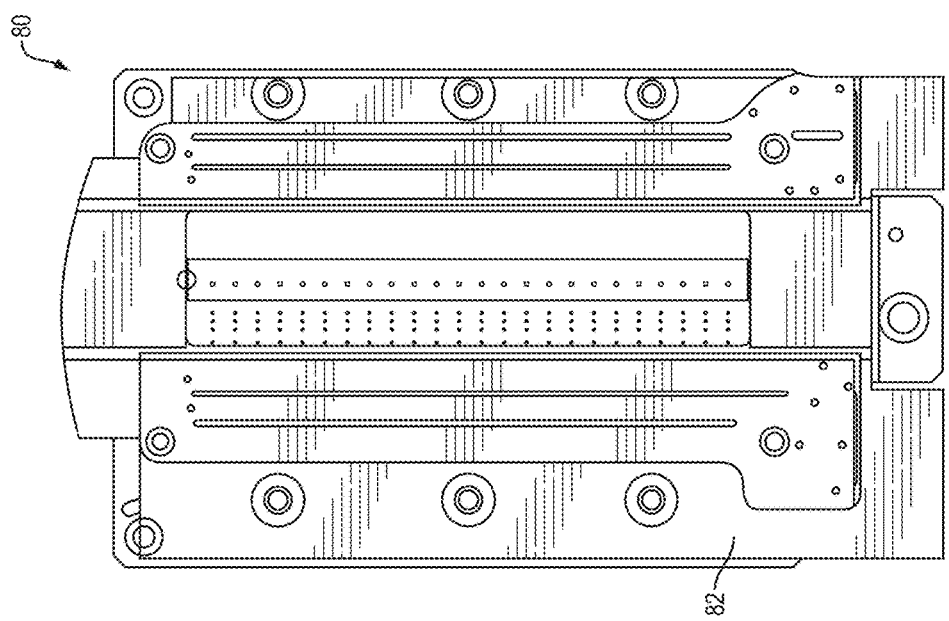
FIG. 7 is a top view of the chip holder and microfluidic device of FIG. 6.

FIG. 5 is a schematic diagram of an exemplary microfluidic system 10, in accordance with some embodiments. The microfluidic system 10 includes receptacle 42 for receiving a microfluidic device, such as microfluidic chip 20 of FIG. 1. In some embodiments, the receptacle 42 receives a microfluidic chip 20 in a holder 80. FIGS. 6 through 8 depict a holder 80 for microfluidic chip 20. Particles and fluid may be supplied to the microfluidic chip 20 from a first side 82 of the holder. The microfluidic chip 20 may be illuminated through an aperture 86 defined in a second side 84 of the holder. In some embodiments, multiple apertures may be defined in holder. For example, a multiple aperture configuration may be aligned with a single fluidic channel, which may enable various pulse detection configurations (e.g. velocity measurements, bar coding, etc.). The multiple aperture configuration may be repeated for the different channels forming an array of apertures that matches the configuration of fluidic channel array. In some embodiments, apertures may be in the form of slots configured to extend across multiple fluidic channels.

Turning again to FIG. 5, the microfluidic system 10 also includes a light source 44 for simultaneously illuminating at least a portion of each of the microfluidics channels 30 (e.g., the portion of each microfluidic channel 30 in the source area 22).

The light source 44 may be a laser, a diode laser, a monochromatic light source, polychromatic light source, or any combination of the aforementioned. As a non-limiting example, the light source 44 may be a Coherent Sapphire 488/200 laser, which is a small, air-cooled optical pumped semiconductor (OPS) device producing about 200 mW, 2 W, or 5 W with minimal optical noise. As another non-limiting example, a diode pumped solid state (DPSS laser may be used, which is capable of generating different wavelengths of light, such as 355 nm at 300 mW or 2 W, or 532 nm at 1 W, 2 W, 5 W, or 10 W for excitation and/or illumination. One skilled in the art will recognize that any suitable light source may be used.

In some embodiments, the microfluidic system 10 includes beam shaping optics 46 for producing and forming one or more beams of light 50. In some embodiments, the one or more beams of light 50 may pass through an optical mask 60 before reaching channel 30. The optical mask 60 may take the form of an array of pinholes with each pinhole corresponding to a channel 30. The light admitted through the optical mask 60 intersects one or more particles 62 conveyed through channel 30 producing optical signals 52, 53, 54. Examples of optical signals that may be produced in optical particle analysis cytometry or sorting when a light beam intersects a particle include, but are not limited to: optical extinction, angle dependent optical scatter, and fluorescent light. Optical extinction refers to the amount of illumination light attenuated by a particle. Angle dependent optical scatter refers to the fraction of light that is scattered or refracted at each angle (theta) away from the incident light beam. Fluorescent light results from light that is absorbed by molecules in, on, or around the particle and re-emitted at a longer wavelength.

The microfluidic system 10 includes an optical system 110 for receiving light 52 emitted from the plurality of micro channels 30. Light 52 emitted from the plurality of micro channels includes light emitting from particles 62 in the micro channels. Exemplary embodiments of optical systems and optical characteristics of some exemplary embodiments are described below with respect to FIGS. 10 through 37. Receptacle 42 or another component of microfluidic system 10 may incorporate one or more stages for positioning the microfluidic chip 20 relative to the optical system 110.

The microfluidic system 10 includes one or more detectors (e.g., photo-detectors 64) for detecting light 56 output from the optical system 110. The light 56 from the optical system may be focused onto optical transmission fibers 66, which transmit the light 56 to the photo-detectors 64. The microfluidic system 10 may include a dedicated optical transmission fiber 66 for each channel 30 in the source area of the microfluidic chip 20. In some embodiments, the microfluidic system may also include an array of in-line optical fiber coupler-splitters 68 to split light 56 from each transmission fiber 66 into multiple output fibers 69. The photo-detectors 64 may be connected to electronics 70 that control and/or receive signals from the photo-detectors 64. Electronics 70 may also control one or more actuators (e.g., actuator 19 of FIG. 4) for sorting particles flowing through the channels 30. A measurement and detection system (e.g., system 76 of FIG. 4) that sends signals to an actuator 19 (see FIG. 4) may include the light source 44, beam shaping-optics 46, the optical system 110, the optical coupler-splitter 68, the photo-detectors 64 and the electronics 70.

The light source 44 may have a suitable wavelength for inducing fluorescence and the optical system may be designed to collect fluorescent light. Fluorescent detection is often used in combination with particles that are labeled with a fluorescent marker, (i.e., an attached molecule that upon illuminating with light of a particular first wavelength produces fluorescent light at another particular second wavelength). If the second wavelength of light is detected, the characteristic is sensed and a signal is raised. Fluorescent detection can also be performed on intrinsically fluorescent particles.

In some embodiments, a microfluidic system may include additional optical systems for collecting and delivering light from the micro channels to detectors. For example, microfluidic system 10 includes a forward scatter system 72 for detecting forward scattering light 53, and a side-scatter system 74 for detecting light 54 scattering at a 90 degree angle from the incoming light 50. Signals 73 from the forward scatter system 72 and signals 75 from the side scatter system 74 may be transmitted the optical coupler-splitter 68 before being transmitted to the photo-detectors 64. The one or more scattering systems may yield information on the size and form of the particles.

As shown, the incident light 50 is provided at about a 45-degree angle relative to the channel 30. The forward scatter light extends in the same direction on the opposite side of the channel 30. As shown, the forward scatter 53 extends at a 45-degree angle from the channel 30. The side scatter 54 extends about 90 degrees from the incident light, providing the fluorescence optics 58 a cone of mechanical freedom 55. In some embodiments, the cone of mechanical freedom 55 provides a 90 degree unobstructed view for the detector in between the forward scatter 53 and side scatter 54.

In some embodiments, optical system 110 may be used for the collection of scattered light (e.g., side scatter) from the light source 44 as well as for collection of light emitted from the particles or from the fluid. Additional details regarding using optical system 110 for collection of scattered light are provided below with respect to FIGS. 14 through 16.

The microfluidic system 10 may also include one or more additional optical systems, which may incorporate microscopes, machine vision systems, etc. In some embodiments, the microfluidic system 10 may further include electronic means for measuring electronic properties of the particles.

Figure 9:
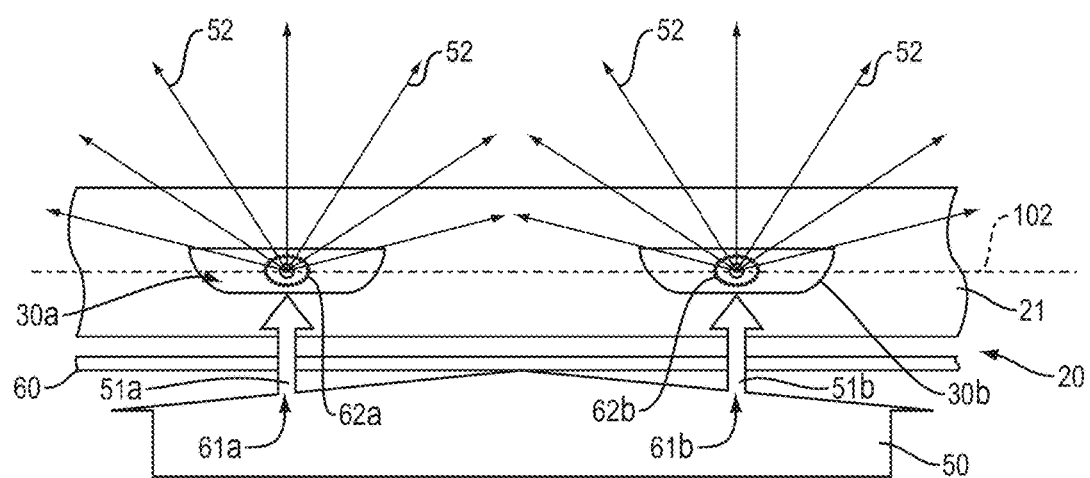
FIG. 9 schematically depicts a cross-section of a portion of the microfluidic chip depicted in FIG. 1.

FIG. 9 is a detail of a cross-section through part of the microfluidic chip 20 depicted in FIGS. 1 and 2 containing a pair of micro channels 30a and 30b. The cross-section is in a plane that cuts through the micro channels and the pinholes 61a, 61b of the mask 60. The incident light 50 is partly blocked by the mask 60 and narrowed to focused beams 51a, 51b defined by each pinhole 61a, 61b. The focused beams 51a, 51b intersect each microchannel 30a, 30b to illuminate the region in which particles 62a, 62b are permitted to flow in a conventional core flow. Excess stray light is blocked by the mask 60, which may be a separate part from the microfluidic chip 20 or may be fabricated on the surface of the microfluidic chip by photolithography or other methods known to those skilled in the art of chip fabrication.

As shown in FIG. 9, light 51a, 51b incident on micro channels 30a, 30b is scattered by, absorbed by and/or emitted by particles 62a, 62b in the micro channels. The scattered/emitted light 52 from the particles 62 is collected by the optical system 110 (see FIGS. 10 and 11). An object plane 102 of optical system 110 (see FIG. 11) passes through the micro channels 30. As illustrated by FIG. 9, particles 62a, 62b in different channels 30a, 30b may be simultaneously emitting/scattering light that is collected by the optical system 110 (see FIG. 11) to monitor particle and or fluid flow through a plurality of micro channels simultaneously.

Although FIGS. 1-9 depict a microfluidic chip 20 and a microfluidic system 10 for particle (e.g. cell) sorting, one skilled in the art will recognize that exemplary optical systems described herein are not limited to use in sorting systems. Exemplary optical systems may be used with other types of microfluidic systems (e.g., microfluidic analysis systems), or any other type of system or application requiring an optical system with a large field of view and a small f-number (e.g., imaging, microarray, sequencing, high throughput screening, other biomedical and diagnostic applications, semiconductor wafer inspection, solar panel inspection, optical display panel imaging, etc.). Fields in which embodiments of optical systems may be used include biomedical, metrology, imaging, optical measurements, machine vision, inspection, manufacturing, and quality control.

Figure 10:
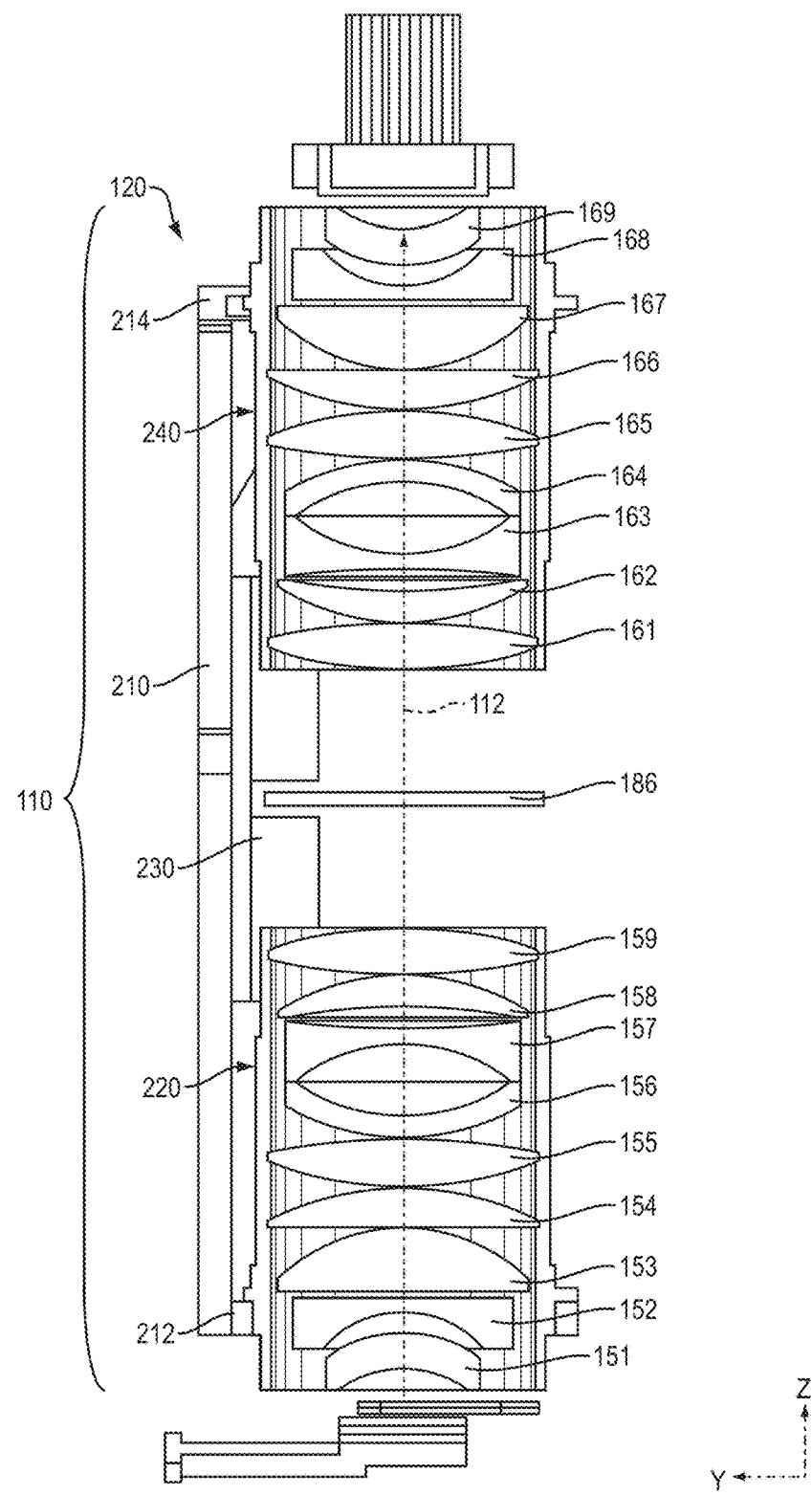
FIG. 10 illustrates a side cross-sectional view of an exemplary optical system for collecting, collimating, and focusing light from a plurality of flow cytometers, in accordance with some embodiments.

An exemplary optical system 110 for collecting and collimating light from micro channels associated with a plurality of flow cytometers is illustrated in FIG. 10. The optical system 110 includes a plurality of optical elements 151, 152, 153, 154, 155, 156, 157, 158, 159, 186, 161, 162, 163, 164, 165, 166, 167, 168, 169 disposed along an optical path 112 of the system and a mounting system 120 for mounting the plurality of optical elements 151 . . . 169 along the optical path 112. Further detail regarding an exemplary mounting system is described below with respect to FIGS. 20-22.

Figure 11:
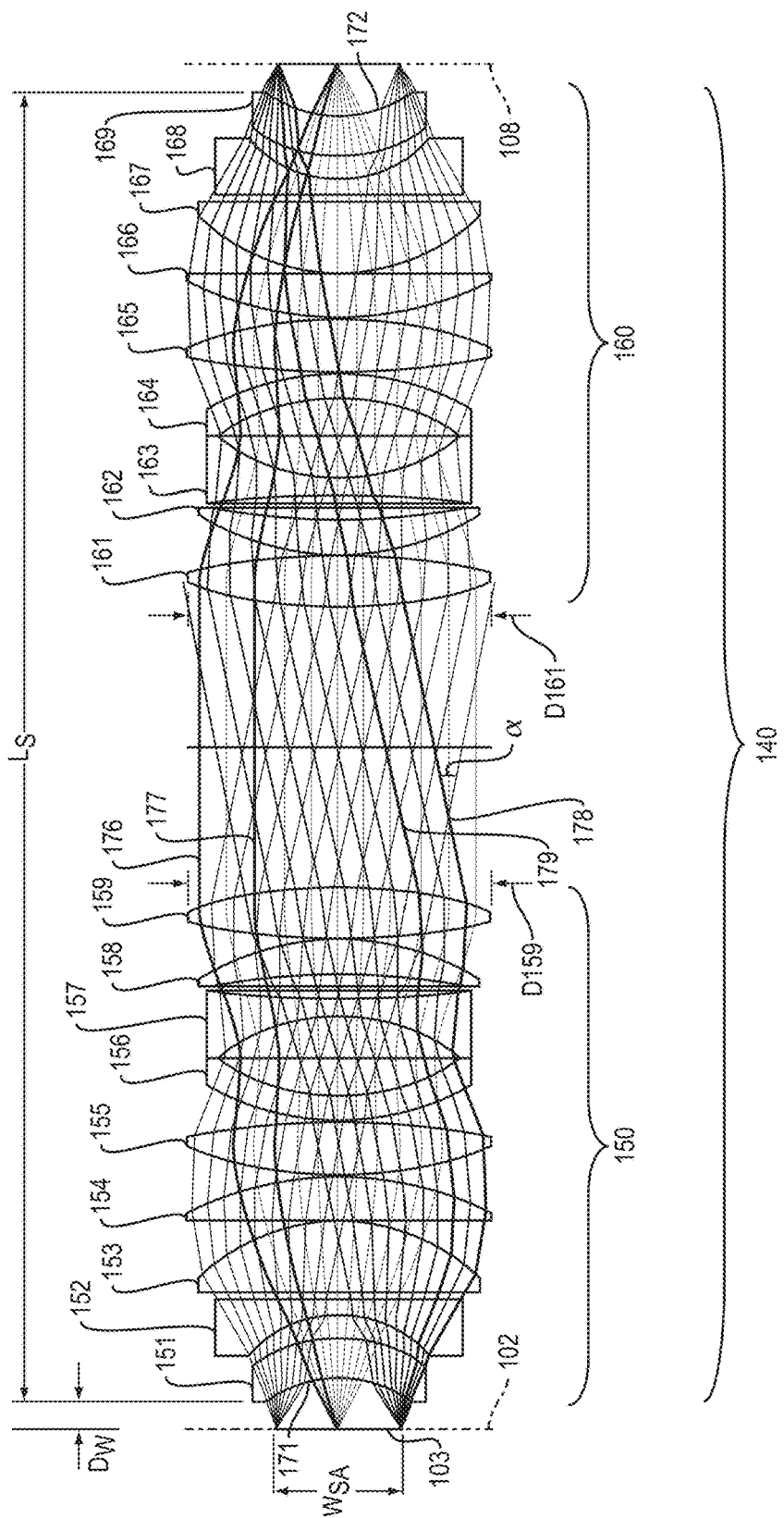
FIG. 11 illustrates a side cross-sectional view of optical elements of the optical system depicted in FIG. 10, including ray traces.

FIG. 11 shows the behavior of the plurality of optical elements 140 in the optical system 110 using ray tracing. For clarity, the mounting system 120 has been omitted. The plurality of optical elements 140 collects light from a source area 103 at the object plane 102 of the optical system and collimates the light. As shown, the plurality of optical elements 120 may include a first set of optical elements (e.g., lenses) 150 that collects and collimates light from the source area 103 and a second set of optical elements (e.g., lenses) 160 that images the light onto an image plane 108. As illustrated by optical paths 176 and 177, light from a central portion of the source area 103 is collected and collimated by the first set of optical elements 150, and then is focused by the second set of optical elements 160 onto the image plane at 108. As illustrated by optical paths 178 and 179 light from an edge portion of the source area 103 is collected and collimated by the first set of optical elements 150, and then is focused by the second set of optical elements 160 onto the image plane at 108.

The first set of optical elements 150 may include a first set of lenses 151, 152, 153, 154, 155, 156, 157, 158 and 159, as shown. The second set of optical elements 160 may include a second set of lenses 161, 162, 163, 164, 165, 166, 167, 168, and 169, as shown.

Although the plurality of optical elements 140 includes a first set of refractive lenses 151 . . . 159 and a second set of refractive lenses 161 . . . 169, in some embodiments, diffractive or reflective elements (e.g., diffractive elements, reflective optics) may be used instead of some or all of the lenses.

The first set of optical elements 150 may include nine or more substantially co-axial lenses that collect and collimate the light, as shown. The second set of optical elements 160 may include nine or more substantially co-axial lenses that focus the collimated light, as shown. In some embodiments, the first set of optical elements and the second set of optical elements may include different numbers of lenses. In some embodiments, the first set of optical elements and the second set of optical elements may each include more or fewer than nine lenses.

For example, in some embodiments, the first set of optical elements 150 may include seven or more substantially co-axial lenses that collect and collimate the light. The second set of optical elements may include seven or more substantially co-axial lenses that focus the light. Example 2, described below with respect to FIG. 23, includes a first set of seven lenses that collect and collimate light from a source area and a second set of seven lenses that focus the collimated light.

In exemplary optical system 110, the last lens 159 along the optical path in the first set of lenses has a diameter $D_{159}$ greater than 60 mm (e.g., between about 65 mm and about 70 mm) and the first lens 161 along the optical path in the second set of lenses has a diameter $D_{161}$ greater than 60 mm (e.g., between about 65 mm and about 70 mm). In some embodiments, $D_{159}$ and/or $D_{161}$ may be greater than 70 mm.

In the exemplary optical system 110, all of lenses 151 . . . 169 are non-aspheric. In other embodiments, some or all of the lenses may be aspherical. In yet further embodiments, some or all of the lenses may be spherical or aspherical.

In the exemplary optical system 110, the first optical element (e.g., lens 151) in the first plurality of optical elements disposed along the optical path has a concave surface 171 facing the source area 103. In the exemplary optical system 110, the last optical element 169 in the plurality of optical elements 160 disposed along the optical path may have a concave surface 172 facing the image plane 108. In other embodiments, the first optical element along the optical path may not have a concave surface facing the source area, and last optical element along the optical path may not have a concave surface facing the source area.

The optical system 110 may have a combination of optical properties that make it particularly well suited for applications involving the collection and collimation of light from a plurality of micro channels associated with a plurality of flow cytometers. For example, optical system 110 collects light over a relatively large area and has a relatively high numerical aperture/low f-number. The optical system may collect light from a source area 103 having a lateral length or width $W_{SA}$ of at least about 25 mm (e.g., within a range of about 25 mm to about 75 mm). The optical system may have an f-number (N) of less than about 1.2 (e.g., within a range of about 0.9 and 1.2) for light from all portions in the source area. Such a low f-number optical system may be particularly useful for low light applications, such as collecting light from fluorescence, luminescence, phosphorescence, scattered light, plasmonic emission, and/or Raman emission.

A working distance $D_w$ between the object plane 102 and the first optical element (e.g., lens 151) along the beam path may be greater than 10 mm (e.g., within a range of about 10 mm to about 30 mm). Such a large working distance may be particularly useful in a flow cytometry system in which particles that emit or scatter light are separated from the optical system by at least fluid in the channel and a top surface of a microfluidic chip.

Due to the symmetric nature of the design, the following aberrations may be canceled: distortion, coma, and/or lateral chromatic aberration, within the limits of the fabrication tolerances of the design. Lens system 110 may have relatively little longitudinal chromatic aberration and relatively little spherical aberration. For example, in FIG. 11, the first set of lenses 150 and the second set of lenses 1610 may form an air-spaced achromatic lens pair. The lens system 110 may have a longitudinal chromatic aberration within a range of about −0.350 mm and about 0.350 mm. The optical system 110 may have a maximum distortion of less than 0.05% (e.g., within a range of about 0.005% and about 0.05%) for light from all points in the source area, see also explanation of FIGS. 26 and 27 below.

The resolution of the optical system may be relatively high. In some embodiments, the optical system 110 may have a resolution of at least 20 μm (e.g., within a range of about 20 μm to about 260 μm) for light from all points in the source area. For example, see the explanation of FIGS. 32 and 33 below.

The lens system 110 may have relatively high transmission for light from all points in the source area 103. In some embodiments, the optical system 110 may have a transmission of at least 70% (e.g., within a range of about 70% to about 95%) over a wavelength range of about 350 nm to about 900 nm.

Further, the output relative illumination may be high for all points in the source area. In some embodiments, the output relative illumination of the optical system 110 may be above 70% (e.g., within a range of about 70% to about 95%) for light from all points in the source area 103. For example, see the description of FIGS. 24 and 25 below.

The point spread function of the lens system 110 for various points across the source area may be characterized through encircled energy. For all light energy incident on an image plane from a point source located in the source area, the encircled energy of the lens system can be described as a percentage of the total energy incident on the source plane that is encircled by a circle of a specified radius around the centroid of the distribution, (e.g., the percentage of light that falls within a circle of radius 100 μm or diameter 200 μm). Alternatively, the encircled energy may be described as a radius (or diameter) of a circle around the centroid of the light distribution that would encircle a specified percentage of the total energy incident on the image plane, (e.g., the radius that encircles 50% of the energy). The encircled energy of the system may depend on the wavelength of the light emitted from the source area.

In some embodiments, the lens system 110 may be configured such that at least 65% of the energy incident on the image plane emitted by a point source in the source area is encircled by a 200 micron diameter circle at the image plane for all points in the source area and for a wavelength within the range of about 540 nm to about 820 nm. In some embodiments, the lens system may be configured such that at least 75% of the energy incident on the image plane from a point source in the source area is encircled by a 200 micron diameter circle for all points in the source area and for a wavelength in the range of about 665 nm to about 820 nm. For example, see the description of FIGS. 28 through 31 below.

Most or all of the transmissive optical elements (e.g., lenses, filters, gratings) in the plurality of optical elements 140 may include materials having relatively low autofluorescence. In some embodiments, each lens in the plurality of optical elements 140 may include a material having an auto-fluorescence within a range of about 20× to about 2× less than BK7 glass. For example, see Table 2 below.

The lens system 110 may have about one to one magnification. For example, the magnification of the optical system may fall within a range of about 0.9995 to about 1.005. In some embodiments, a variation in the magnification across the lens system may fall within a range of +/−5%. For example, see the description of FIGS. 32 and 33 below.

The lens system may have a relatively small depth of field. In some embodiments, a depth of field of the optical system may be within a range of about −0.250 μm and about 250 μm. For example, see the description of FIGS. 34-37 below.

The optical system may have a relatively short length $L_s$ measured as a distance between the first optical element (e.g., lens 151) in the first set of optical elements 150 along the beam path 112 and the last optical element (e.g., lens 169) in the second set of optical elements 160 along the beam path 112. For example, the length $L_s$ may be less than about to 800 mm (e.g., within a range of about 500 mm to about 800 mm).

Figure 12:
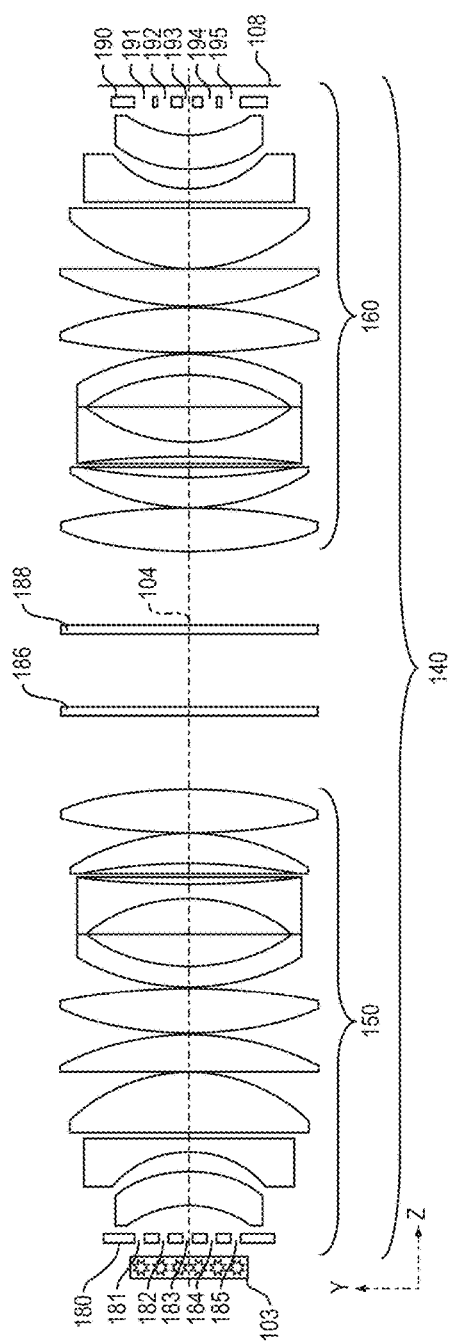
FIG. 12 schematically depicts a side cross-sectional view of a plurality of optical elements of the optical system depicted in FIG. 11 including an array of input apertures, an array of output apertures, a filter, and a grating, in accordance with some embodiments.

FIG. 12 illustrates additional optical elements that may be included in the optical system 110. For clarity, mounting system 120 has been omitted. The plurality of optical elements 140 may include one or more diffractive elements, such as a diffraction grating 188. The diffraction grating 188 (reflective or transmissive) may be placed in between the first set of optical elements 150 and the second set of optical elements 160. Collimated light from the lens assembly first set of optical elements 150 will then be spectrally dispersed by the grating 188 and refocused by the second set of optical elements 160. The spectrum of the source is distributed in the image plane along the dispersive axis of the grating. Although the first set of optical elements 150 and the second set of optical elements 160 share a same central axis 104 as shown, in some embodiments, the second set of optical elements 160 may have a central axis at an angle to the central axis 104 of the first set of optical elements 150 (e.g., when using a transmission or reflection diffraction grating, and/or selectively imaging a non-zero diffraction order). For example, the second set of optical elements 150 may be arranged for imaging first order diffraction spots.

The plurality of optical elements 140 may include an optical element 180 defining an array of input apertures 181, 182, 183, 184, 185 disposed in proximity to the source area 103. Each input aperture 181 . . . 185 may align with a channel 30 in the source area 103. For illustrative purposes, only five input apertures are depicted even though microfluidic chip 20 includes twenty-four or more (e.g. 72, or 144) channels 30 in the source area. Each input aperture 181 . . . 185 may function to reduce the incidence of stray light (e.g., light from sources other than the microchannel) on the first set of optical elements 150.

The plurality of optical elements 140 may include an optical element 190 defining an array of output apertures 191, 192, 193, 194, 195 disposed in proximity to an image plane 108. For illustrative purposes, only five input apertures are depicted even though microfluidic chip 20 includes twenty-four or more channels 30 in the source area. The output apertures 191 . . . 195 may function to at least partially block light emitted from points in the source area that are not at the focal plane.

Figure 13:
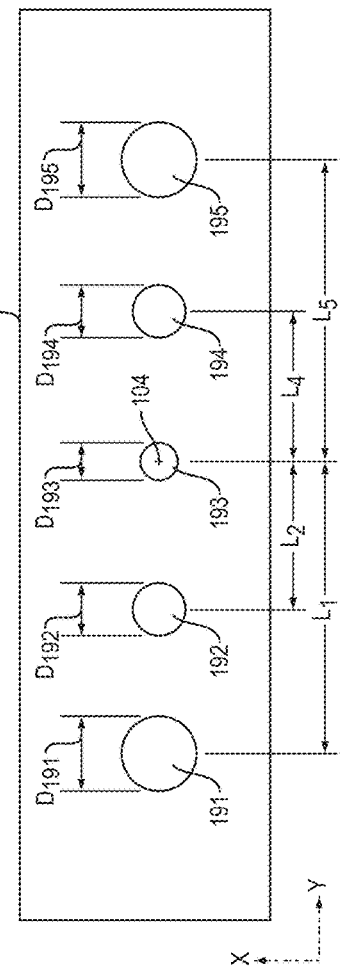
FIG. 13 schematically depicts a front view of the output apertures of FIG. 12.

The diameter of each output aperture may increase with an increasing lateral distance between the center of the output aperture and the central axis as illustrated by FIG. 13. For example, output aperture 193, which is not laterally displaced from the central axis 104, has a diameter $D_{193}$. Output aperture 192, which is displaced from the central axis 104 by a distance $L_2$, has a diameter $D_{192}$ larger than the diameter of the central output aperture $D_{193}$. Similarly, output aperture 194, which is displaced from the central axis 104 by a distance $L_4$, has a diameter $D_{194}$ larger than the diameter of the central output aperture $D_{193}$. Output aperture 191, which is displaced from the central axis 104 by a distance $L_1$, has a diameter $D_{191}$ larger than the diameters of the output apertures with smaller lateral displacements (e.g., $D_{192}$, $D_{193}$, $D_{194}$. Similarly, output aperture 195, which is displaced from the central axis 104 by a distance $L_5$, has a diameter $D_{193}$ larger than the diameters of the output apertures with smaller lateral displacements (e.g., $D_{192}$, $D_{193}$, $D_{194}$).

In some embodiments, the diameter of each output aperture may be proportional to a selected encircled energy diameter for a corresponding position in the image plane. For example, an output aperture centered at position in the image plane, which corresponds to a particular position in the source area, may be dimensioned to transmit 85% of the energy incident on the image plane from a point source located at the particular position in the source area that emits a specified wavelength or range of wavelengths of light. Further details regarding encircled energy for various positions in the image plane for optical systems are described below with respect to FIGS. 28-31.

In some embodiments, a diameter of each aperture in the array of output apertures is about equivalent.

The plurality of optical elements 140 may include one or more filters. For example, a filter 186 may be positioned along the beam path after the first set of optical elements 150 and before the second set of optical elements 160, as shown. In other embodiments, a filter may be positioned at one or more different locations along the beam path, which may depend on the angle of incidence limitation of the filter. Two filters may be positioned at symmetrical locations in the system to maintain optical symmetry of the design. Many different types of filters may be included in the optical system (e.g., bandpass, notch, line, lowpass, highpass, cut-off, multi-band, polarizer, holographic, etc.).

Figure 14:
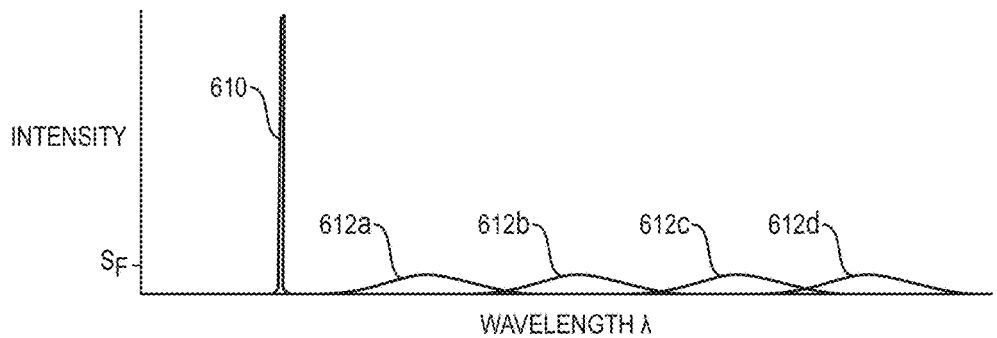
FIG. 14 is a schematic of light intensity versus wavelength for an optical system not including a low pass filter.
Figure 15:
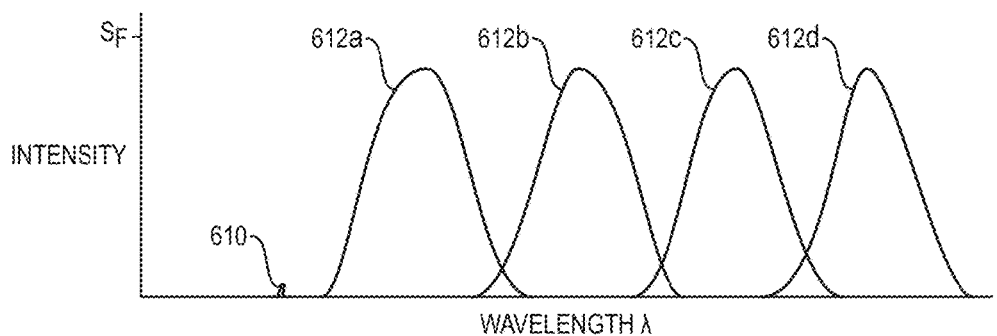
FIG. 15 is a schematic of light intensity versus wavelength for an optical system including an OD6 low pass filter.

A filter, such as a long pass filter, may be used to filter out wavelengths of light associated with the light source 44 (e.g., laser) to increase the ratio of the fluorescence signals to the illumination light from the particles or from the fluid. FIG. 14 schematically depicts light intensity through optical system 110 without a long pass filter. As shown in FIG. 14, signals 612a-612d associated with fluorescence are several orders of magnitude less than a signal 610 associated with the light source (e.g., laser). The relatively large light source signal 610 can lead to saturation of detectors and optical cross-talk between signals associated with different channels. FIG. 15 schematically depicts light intensity through the optical system 110 when a long pass filter having an optical density of 6 or greater for light of the illumination wavelength is used. Note that in FIG. 15, the intensity axis has a larger scale. As illustrated, when using a long pass filter having an optical density of 6 or greater for light of the illumination wavelength, the fluorescence signals 612a-612d are no longer overwhelmed by the light source signal 610.

Figure 16:
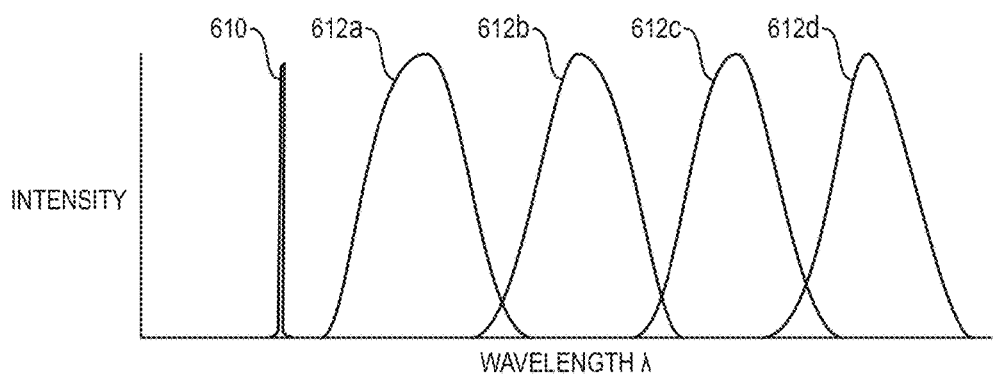
FIG. 16 is a schematic of light intensity versus wavelength for an optical system including a filter that partially transmits light of wavelength 532 nm.

In some embodiments, a partial transmission filter (e.g., a low optical density long pass filter) is used to attenuate the light source signal 610 to an intensity level comparable to the fluorescence signals and transmit sufficient light source signal 610 to allow scattering measurements based on the scattered light source signal 610. Such a partial transmission filter matched to the intensity of the incident light source signal (relative to the incident florescence signal) and wavelength of the light source signal that yields a transmitted light source intensity of the same order of magnitude as one or more transmitted fluorescence light intensities is referred to as a "leaky" filter herein. For example, FIG. 16 schematically depicts light intensity through the optical system 110 including a leaky filter (e.g., a long pass optical filter of about OD3). The optical density range for a leaky filter will depend on the relative magnitudes of the light source signal and the fluorescence signals of interest. In some embodiments, the optical density of the leaky filter is sufficient for the transmitted light source signal and a transmitted fluorescence signal of interest to be about the same order of magnitude in intensity.

Figure 17:
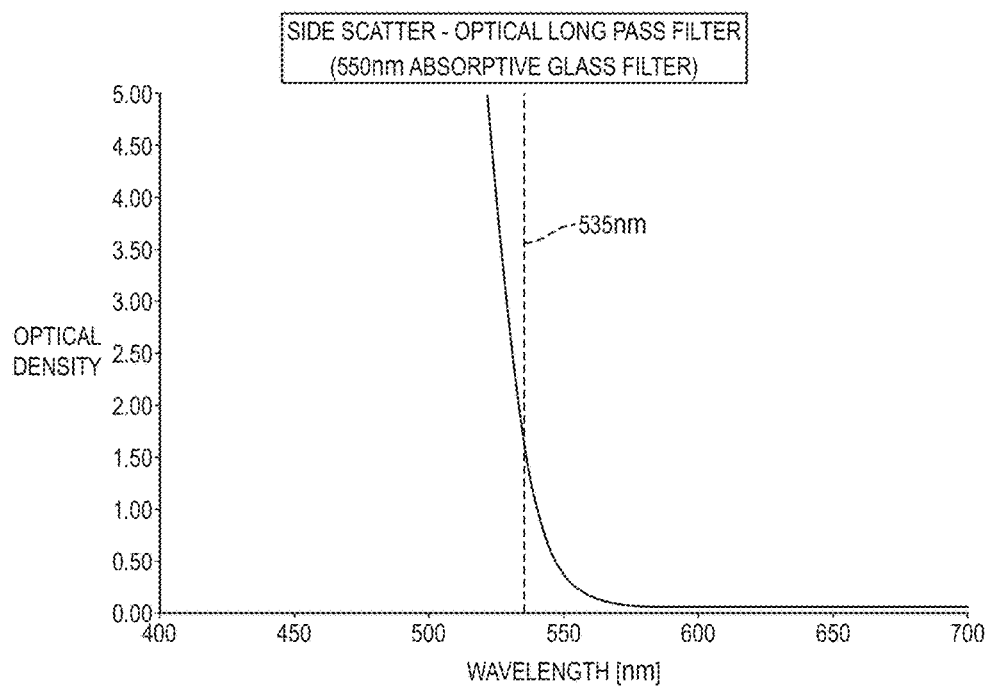
FIG. 17 is a graph of optical density versus wavelength for a 550 nm absorptive glass long pass filter that partially transmits light of wavelength 532 nm, in accordance with some embodiments.
Figure 18:
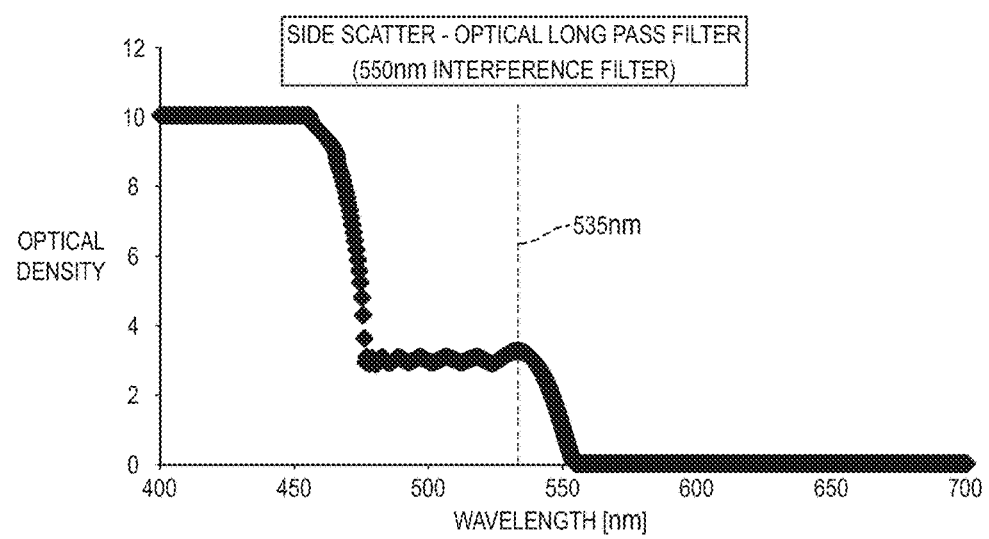
FIG. 18 is a graph of optical density versus wavelength for a 550 nm step interference filter that partially transmits light of wavelength 532 nm, in accordance with some embodiments.

FIGS. 17 and 18 are graphs of optical density versus wavelength for example leaky filters. FIG. 17 is a graph of optical density versus wavelength for a 550 nm long pass absorptive glass filter. For a light source with wavelength 532 nm, the filter has an optical density of about 1.7, which drops off rapidly with increasing wavelength. In some embodiments, the optical density of 1.7 attenuates the light source signal to a level suitable for scattering measurements that is also comparable to an expected signal level of the longer wavelength fluorescence.

FIG. 18 is a graph of optical density versus wavelength for a 550 nm long pass step interference filter. For a light source with wavelength 532 nm, the filter has an optical density of about 3, with a very low optical density for wavelength longer than 550 nm. In some embodiments, the optical density of 3 attenuates the light source signal to a level suitable for scattering measurements that is also comparable to an expected signal level of the longer wavelength fluorescence.

Although FIGS. 17 and 18 refer to leaky filters that are long pass filters, other embodiments may employ other types of filters as leaky filters (e.g., notch filters, band pass filters, short pass filters, etc.).

Turning again to FIG. 12, although the plurality of optical elements 140 is shown including a filter 186 and a transmission grating 188, in some embodiments, the plurality of optical elements includes a filter, but not a transmission grating. In some embodiments, the plurality of optical elements includes a transmission grating, but not a filter.

In some embodiments in which the light from the source area is at least partially coherent light, an array of apertures may be positioned after a first set of optical elements to select one or more Fourier components of the light for imaging. In such an embodiment, a second set of optical elements may have some other position, geometry, and/or configuration, or may be omitted.

In an exemplary optical system 110, the first set of optical elements 150 and the second set of optical elements 160 may form an air-spaced achromatic lens pair. However, in other embodiments, a first set of optical elements and a second set of optical elements need not form an achromatic lens pair. For example, in some embodiments, the second set of optical elements may have a different configuration of elements than the first set, may include a different number of optical elements than the first set and/or may include different types of optical elements than the first set.

In some embodiments, the optical system may be telecentric. For example, the optical system may be object-space telecentric, image-space telecentric or double telecentric.

Although exemplary optical system 110 includes a first set of optical elements 150 for collecting and collimating light and a second set of optical elements 160 for focusing the light, in some embodiments, the optical system may only include the first set of optical elements. For example, one or more additional optical systems may be employed for focusing the collimated light (e.g., each channel in the source area may have its own optical system for focusing the collimated light from the first set of optical elements). In some embodiments, the first set of optical elements may collect light, but not collimate the light.

Figure 20:
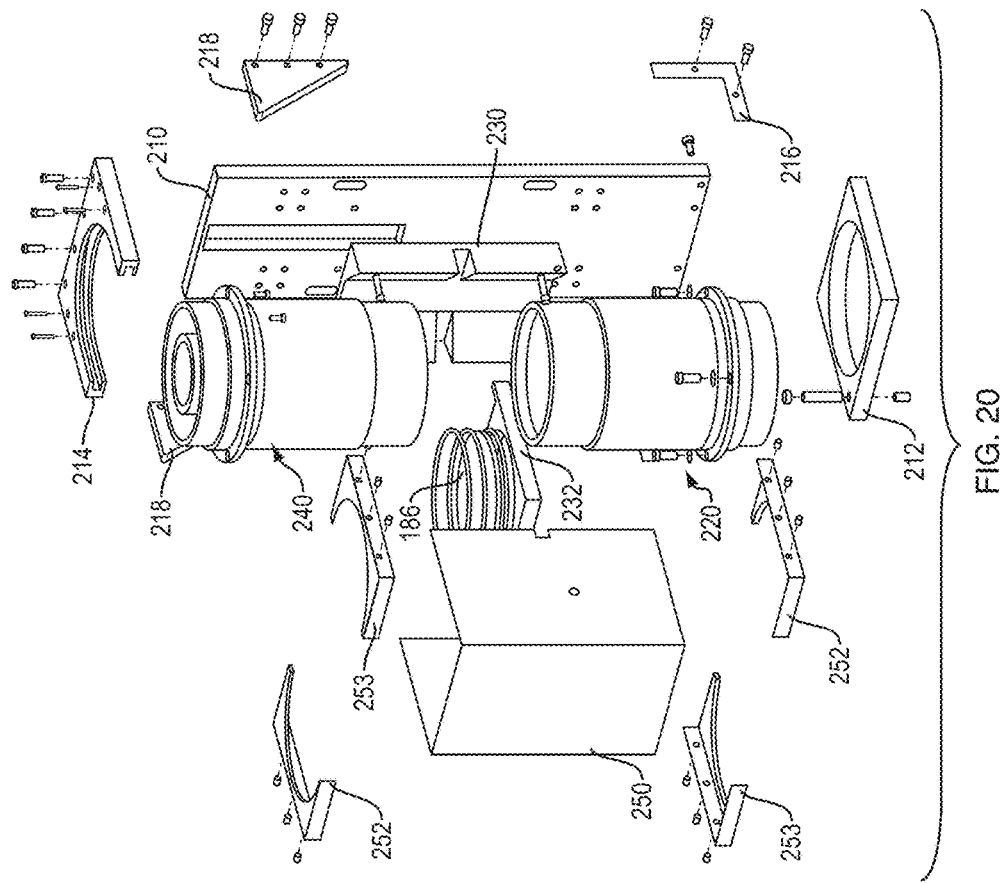
FIG. 20 is an exploded perspective view of the optical system depicted in FIG. 19 showing components of the mounting system.
Figure 19:
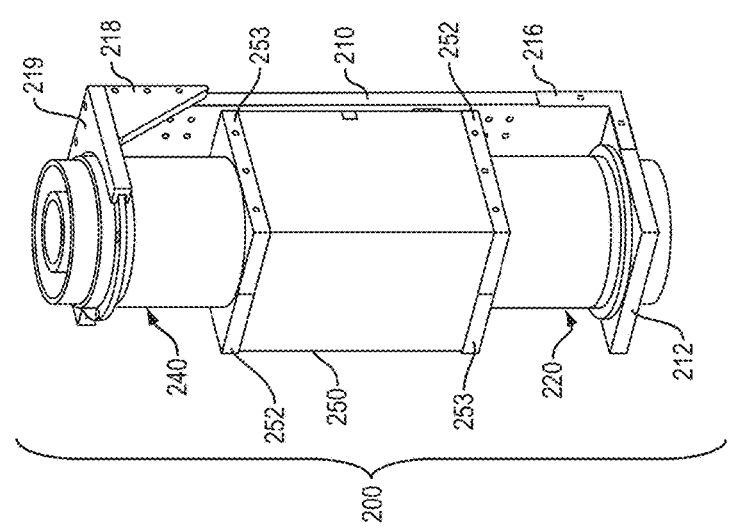
FIG. 19 is a perspective view of the optical system depicted in FIG. 10.
Figure 21:
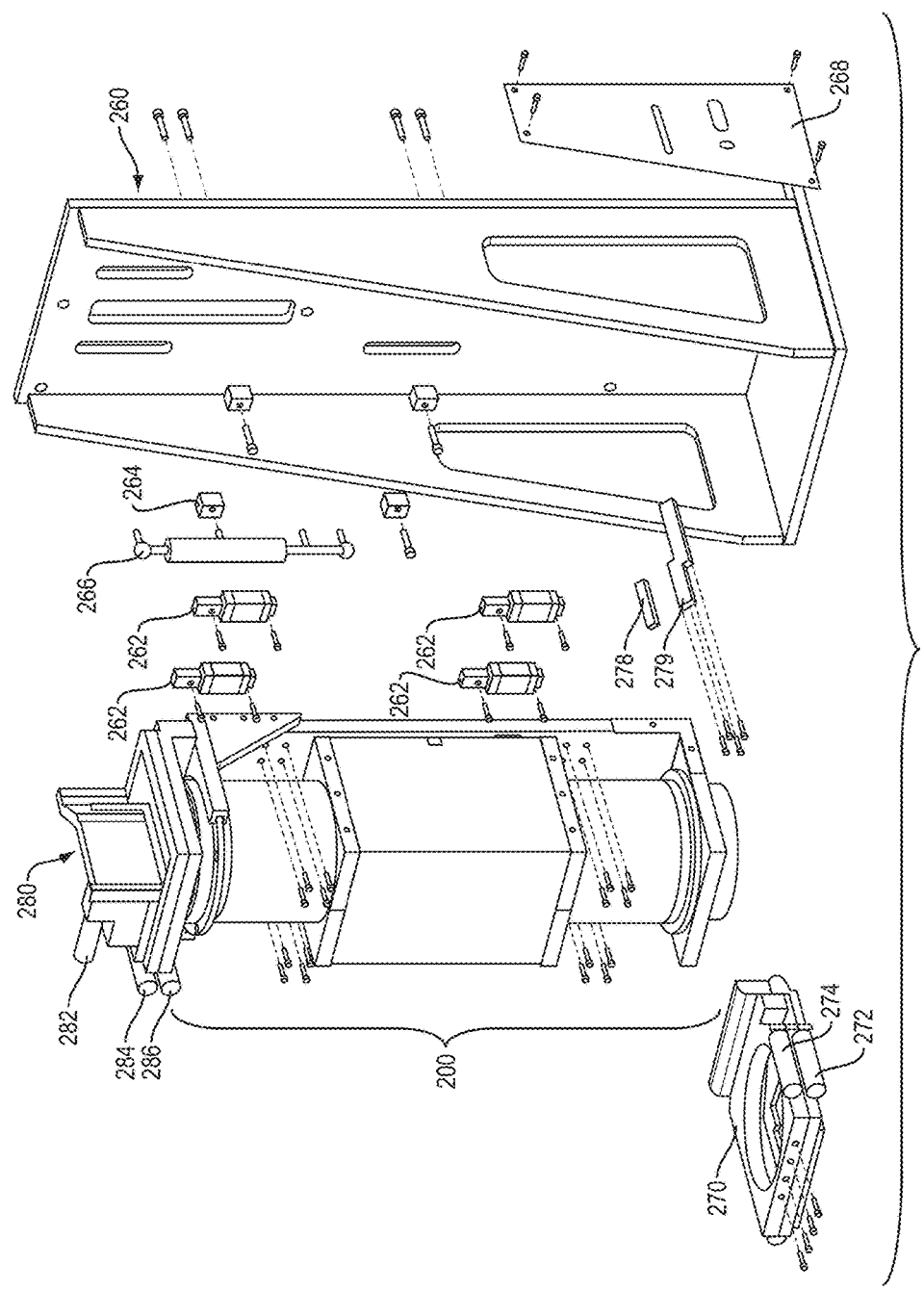
FIG. 21 is an exploded perspective view of additional mounting components for integrating the optical system into a microfluidic system, in accordance with some embodiments.

FIGS. 19 through 21 provide additional views of the optical system 110 that illustrate the mounting system 120. The first set of optical elements 150 (e.g., lenses 151 . . . 159) may be mounted together in a first assembly 220 and the second set of optical elements 170 (e.g., lenses 161 . . . 169) may be mounted together in a second assembly 240 (see also FIG. 10). Each assembly may maintain the alignment and spacing of the optical elements in the assembly relative to each other.

The mounting system 110 may include a backplate 210 to which the first assembly 220 and the second assembly 240 are mounted to maintain the alignment and spacing of the first assembly 220 relative to the second assembly 240. The mounting system 110 may include various components for mounting the first assembly 220 and the second assembly 240 to the backplate 210, such as a bottom plate 212, a top plate 214, a lower gussett 216 and an upper gussett 218 (see also FIG. 10).

The mounting system 110 may further include one or more components for positioning one or more filters and/or gratings between the first assembly 220 and the second assembly 240. For example, mounting system 110 includes a V-block 230, which attaches to the backplate 210, for positioning a filter mount 232 for the long pass filter 186 between the first assembly 220 and the second assembly 240 (see also FIG. 10). The mounting system may also or alternatively include components for positioning one or more filters and/or gratings before the first assembly 220 and/or after the second assembly 240.

The mounting system 120 may include various components for blocking stray light. For example, the mounting system 120 may include a light block shield 250 and light block covers 252, 253, for blocking stray light between the first assembly 220 and the second assembly 240. In FIG. 10 described above, light blocking components were omitted for clarity.

The components in FIGS. 19 and 20 may be described as an optical assembly stage 200 that collects and collimates light from a source area of a microfluidic chip and focuses the light for imaging (e.g. imaging onto optical fibers). FIG. 21 illustrates components that may be included in the mounting system 120 in addition to the optical assembly stage 200. For example, the mounting system 120 may include an optical backplane 260 for mounting and positioning the optical assembly stage 200 relative to other components of the microfluidic system 10. The mounting system 120 may include guides 262, blocks 264 and one or more springs 266 for mounting the optical assembly stage 200 to the optical backplane 260. A panel cable mount and light block 268 may be also be included in the mounting system 120.

The mounting system 120 may include components for adjusting relative positions between the optical assembly stage 200 and other components of a flow cytometry system. For example, mounting system 120 may include a collection assembly 270 including one or more stages 272, 274 for adjusting a relative linear position and/or a relative angular position between the channels 30 of the microfluidic chip 20 and the optical system assembly 200. As to another example, mounting system 120 may include an output assembly 280 including one or more stages 282, 284, 286 for adjusting relative linear positions and/or relative orientations between the optical system assembly 200 and a set of optical fibers (not shown).

The mounting system 120 may also include components for illuminating the source area. For example, mounting system 120 may include a V-groove mirror 278 for directing light into a source area and V-groove mirror mount 279.

Although exemplary optical system 110 is described in the context of a microfluidic sorting system, one of ordinary skill in the art will appreciate that embodiments of optical systems may be employed for any applications requiring a large object area, low f-number optical system.

Example Optical System A

An example optical system including eighteen lenses (Optical System A) was designed constructed in accordance with some embodiments. The performance of Optical System A was evaluated both through modeling and measurements of performance of the optical system. As shown in the cross-sectional view of FIG. 22, Optical System A 300 includes a first optical assembly 310 with nine lenses (311 . . . 319) and a second optical assembly 340 with nine lenses (341 . . . 349). For evaluation, the first optical assembly 310 and the second optical assembly were separated by a distance $D_{300}$ of 149.17 mm. In use, a filter 302 may be positioned between the first optical assembly 310 and the second optical assembly 340. A total length of the optical assembly $L_{300}$ was 695.33 mm. For clarity, mounting components for connecting the first optical assembly 310, the second optical assembly 340, and the filter 302 have been omitted from FIG. 22.

The properties of each lens, and the arrangement of the lenses with respect to each other, the source area (object), and the image plane, appear below in Table 1. All of the surfaces of the lenses in the first optical assembly 310 and the second optical assembly 340 are planar or have spherical curvature. All of the lenses are made of materials having low autofluorescence, e.g., having an autofluorescence levels 20× to about 2× less than BK7 glass. An entry "N/A" for "Material" in Table 1 indicates that the "Thickness or Distance" value is a distance between optical elements. An entry for "Material" that is not "N/A" indicates that the "Thickness or Distance" value is a thickness of an optical component. PYREX is a trademark of Corning Inc. for clear, low-thermal-expansion borosilicate glass.

TABLE 1

Components of Optical System A

| Surface Ref. No. | Radius (mm) | Thickness or Distance (mm) | Material | Diameter (mm) |
|---|---|---|---|---|
| Object Plane | N/A | 0.05 | Seawater | 65 |
| Channel Surface (CS$_1$) | Infinity | 0.75 | PYREX | 67 |
| Cartridge Surface (CS$_2$) | Infinity | 26.61 | N/A | 67 |
| 321 | −68.10063 | 20.80515 | S-LAL18 | 75.9017 |
| 322 | −76.61982 | 12.33964 | N/A | 92.09734 |
| 323 | −65.22603 | 9.65448 | S-TIM28 | 96.10586 |
| 324 | −1131.902 | 2.346531 | N/A | 129.3912 |
| 325 | −2928.79 | 38 | S-LAH65 | 138.1891 |
| 326 | −102.9825 | 0.5 | N/A | 146.5246 |
| 327 | −1915.282 | 22 | S-FPL51 | 157.569 |
| 328 | −180.5367 | 0.3 | N/A | 158.9977 |
| 329 | 214.4746 | 29 | S-FPL51 | 157.898 |
| 330 | −391.0775 | 0.3 | N/A | 156.2838 |
| 331 | 142.5159 | 13 | S-LAH65 | 139.7803 |
| 332 | 112.9747 | 42 | N/A | 127.923 |
| 333 | −106.2333 | 9.65448 | S-TIM28 | 127.5537 |
| 334 | 691.7722 | 11.88346 | N/A | 140.2347 |
| 335 | −394.9692 | 19 | S-PHM52 | 141.9003 |
| 336 | −139.9513 | 0.482724 | N/A | 145.3962 |
| 337 | 395.6249 | 27 | S-PHM52 | 157.5987 |
| 338 | −261.7828 | 72.09495 | N/A | 159.0429 |
| 302 | Infinity | 5 | Silica | 160 |
| 303 | Infinity | 72.09495 | N/A | 158.9803 |
| 351 | 261.7828 | 27 | S-PHM52 | 158.9176 |
| 352 | −395.6249 | 0.482724 | N/A | 157.5743 |
| 353 | 139.9513 | 19 | S-PHM52 | 146.4676 |
| 354 | 394.9692 | 11.88346 | N/A | 143.2976 |
| 355 | −691.7722 | 9.65448 | S-TIM28 | 141.882 |
| 356 | 106.2333 | 42 | N/A | 128.7219 |
| 357 | −112.9747 | 13 | S-LAH65 | 128.7802 |
| 358 | −142.5159 | 0.3 | N/A | 140.732 |
| 359 | 391.0775 | 29 | S-FPL51 | 157.9313 |
| 360 | −214.4746 | 0.3 | N/A | 159.4169 |
| 361 | 180.5367 | 22 | S-FPL51 | 159.6 |
| 362 | 1915.282 | 0.5 | N/A | 158.855 |

TABLE 1-continued

Components of Optical System A

| Surface Ref. No. | Radius (mm) | Thickness or Distance (mm) | Material | Diameter (mm) |
|---|---|---|---|---|
| 363 | 102.9825 | 38 | S-LAH65 | 147.3643 |
| 364 | 2928.79 | 2.346531 | N/A | 139.3445 |
| 365 | 1131.902 | 9.65448 | S-TIM28 | 130.2648 |
| 366 | 65.22603 | 12.33964 | N/A | 96.37122 |
| 367 | 76.61982 | 20.80515 | S-LAL18 | 92.28374 |
| 368 | 68.10063 | 26.9694 | N/A | 75.91994 |
| Image Plane | Infinity | N/A | N/A | 65.12292 |

Figure 22:
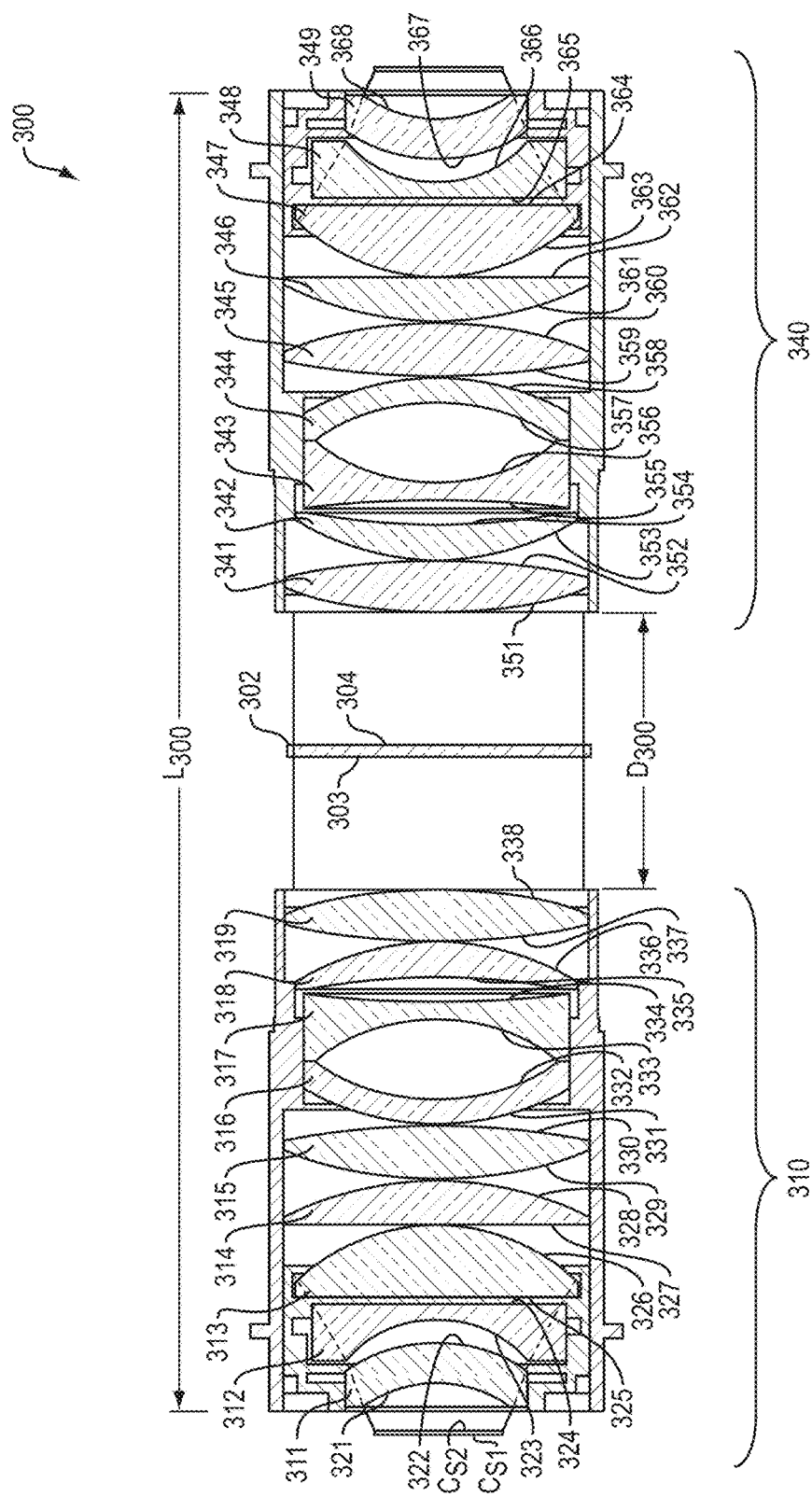
FIG. 22 is a side cross-section view of example Optical System A including eighteen lenses.

As indicated by Table 1 and shown in FIG. 22, the first lens 311 in the first optical assembly has a concave surface 321 facing the object plane and the last lens 349 in the second optical assembly has a concave surface 368 facing the image plane. The last lens 319 in the first optical assembly has a diameter of about 159 mm and the first lens 341 in the second optical assembly has a diameter of about 159 mm.

The materials listed above are offered by the Ohara Corporation. Table 2 below shows the correspondence between glasses offered by the Ohara Corporation and glasses offered by Schott North America, Inc., as well as a brief description of the material. Detailed optical properties of each material may be found in the corresponding Schott Optical Glass Data Sheets, which are available through the web site of Schott North America, Inc.

PYREX is a trademark of Corning Inc. for clear, low-thermal-expansion borosilicate glass.

TABLE 2

Lens Materials for Optical Systems A and B

| Ohara Type | Schott Type | Description |
|---|---|---|
| S-FPL51 | N-PK52A | phosphate crown |
| S-PHM52 | N-PSK53 | dense phosphate crown |
| S-TIM28 | N-SF8 | dense flint |
| S-TIH1 | N-SF1 | dense flint |
| S-LAL18 | N-LAK34 | lanthanum crown |
| S-LAH65 | N-LASF44 | lanthanum dense flint |
| NSL-33 | KF3 | crown flint |
| PYREX | BF33 | borosilicate |

Example Optical System B

Figure 23:
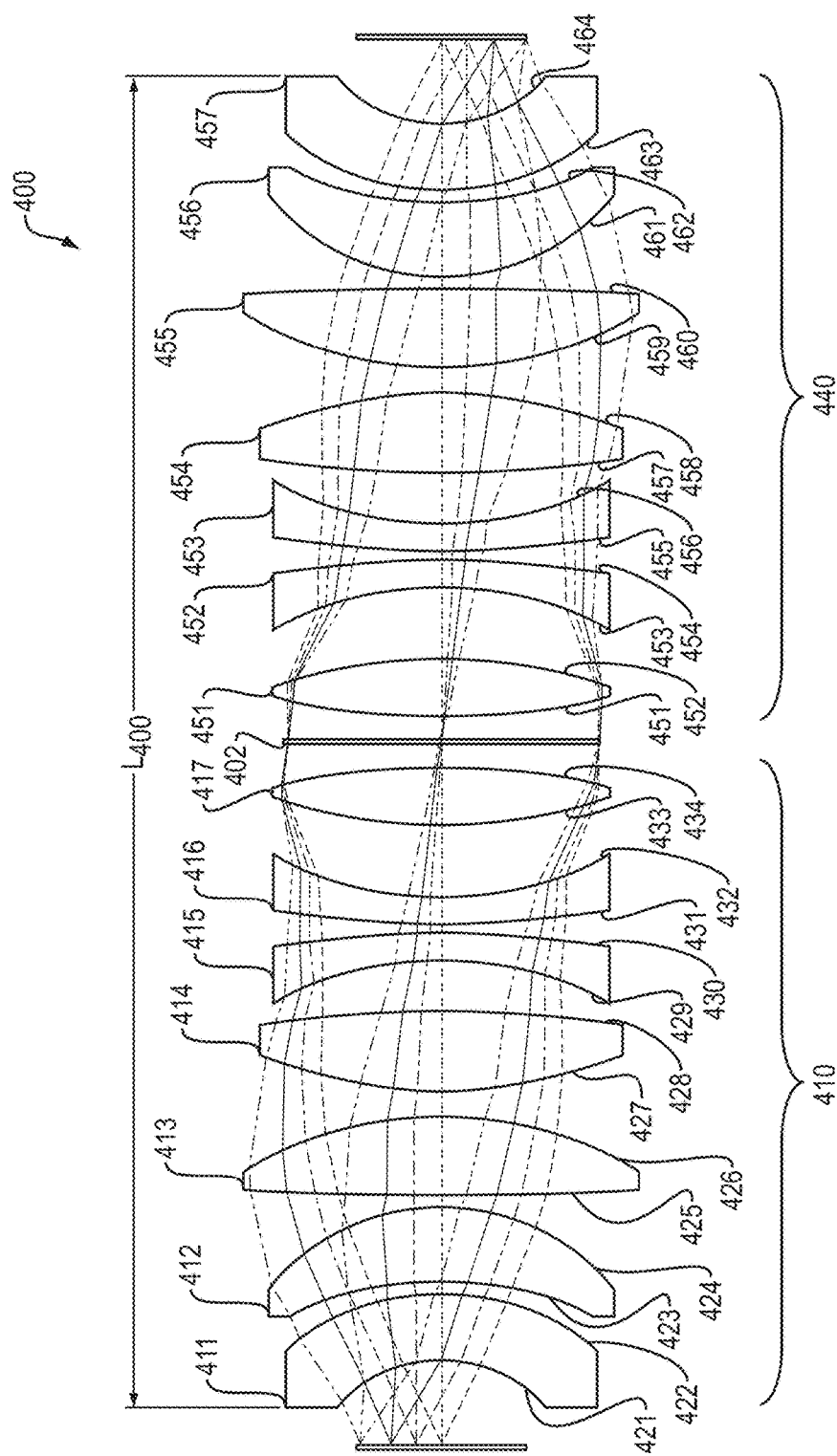
FIG. 23 is a side cross-section view of example Optical System B including fourteen lenses showing ray traces.

An example optical system including 14 lenses (Optical System B) was designed in accordance with some embodiments. The performance of Optical System B was evaluated through modeling. As shown in the cross-sectional view of FIG. 23, Optical System B 400 includes a first optical assembly 410 with seven lenses (411 . . . 417) and a second optical assembly 440 with seven lenses (341 . . . 347). In FIG. 23, components of the mounting system are omitted for illustrative purposes. A total length $L_{400}$ of Optical System B 400 is 495.71 mm. In use, a filter may be positioned between the first optical assembly 410 and the second optical assembly 440. All of the surfaces (421 . . . 464) of the lenses in the first optical assembly 410 and the second optical assembly 440 are planar or have spherical curvature. All of the lenses are made of materials having relatively low autofluorescence 20×-2× less than BK7

Table 3 below includes the properties of each lens, and the arrangement of the lenses with respect to each other, the source area (object) and the image plane.

TABLE 3

Components of Optical System B

| Surface Ref. No. | Radius (mm) | Thickness or Distance (mm) | Material | Diameter (mm) |
|---|---|---|---|---|
| Object Plane | N/A | 0.25 | N/A | 65 |
| Channel Surface (CS$_1$) | Infinity | 0.7 | KF3 (Schott) | 65.01284 |
| Cartridge Surface (CS$_2$) | Infinity | 32.2233 | N/A | 75.07627 |
| 421 | −49.17 | 25.1 | S-TIH1 | 76 |
| 422 | −80.295 | 5 | N/A | 110 |
| 423 | −126.9 | 28.9 | S-PHM52 | 120 |
| 424 | −88.88 | 5 | N/A | 136 |
| 425 | 3567 | 30 | S-PHM52 | 154 |
| 426 | −164.59 | 23.375 | N/A | 154 |
| 427 | 237.9 | 30 | S-PHM52 | 144 |
| 428 | −258.8 | 17.63 | N/A | 144 |
| 429 | −125.02 | 9.2 | S-T1H1 | 128 |
| 430 | −374.7 | 5 | N/A | 134 |
| 431 | 332 | 9.2 | S-T1H1 | 128 |
| 432 | 123.41 | 26.71 | N/A | 120 |
| 433 | 161.97 | 22.7 | S-PHM52 | 128 |
| 434 | −707.7 | 20 | NA | 128 |
| 451 | 707.7 | 22.7 | S-PHM52 | 128 |
| 452 | −161.97 | 26.71 | N/A | 128 |
| 453 | −123.41 | 9.2 | S-T1H1 | 120 |
| 454 | −332 | 5 | N/A | 128 |
| 455 | 374.7 | 9.2 | S-T1H1 | 134 |
| 456 | 125.02 | 17.63 | N/A | 128 |
| 457 | 258.8 | 30 | S-PHM52 | 144 |
| 458 | −237.9 | 23.375 | N/A | 144 |
| 459 | 164.59 | 30 | S-PHM52 | 154 |
| 460 | −3567 | 5 | N/A | 154 |
| 461 | 88.88 | 28.9 | S-PHM52 | 136 |
| 462 | 126.9 | 5 | N/A | 120 |
| 463 | 80.295 | 25.1 | S-T1H1 | 110 |
| 464 | 49.17 | 32.701 | N/A | 76 |
| Image Plane | Infinity | N/A | N/A | 65.38895 |

In Table 3, an entry "N/A" for "Material" indicates that the "Thickness or Distance" value is a distance between optical elements. An entry for "Material" that is not "N/A" indicates that the "Thickness or Distance" value is a thickness of an optical component.

Comparison of Example Optical System A and Example Optical System B

In Table 4 below, various optical properties and characteristics of Optical System A and Optical System B are summarized for comparison. As shown in Table 4, both Optical System A and Optical System B have a low f-number. Optical System A has an f-Number of 1.01 for light from the center of the source area. Optical System B has an f-Number of 1.16 for light from the center of the source area.

TABLE 4

Summary of Optical Properties

| Property | Optical System A | Optical System B |
|---|---|---|
| f-Number (center) | 1.01 | 1.16 |
| Working Distance (mm) | 14/26 (Center/Edge) | 12/30 (Center/Edge) |
| Relative Illumination (center/edge) | center: 100% edge: 78% | center: 92% edge: 100% |
| Max Distortion (%) | 0.0005% | 0.001% |
| Encircled Energy within 100 μm diameter spot | 550 nm: 70-100% 675 nm: 100% 810 nm: 90-100% | 550 nm: not calculated 675 nm: 80-100% 810 nm: not calculated |
| Spot Size (μm) 50 μm, 50% psf 90% psf | 50 μm, 50% psf: 10-100 50 μm, 90% psf: 20-260 400 μm: 90% psf: 120-360 | 50 μm, 50% psf: 60-100 50 μm, 90% psf: 140-240 400 μm, 90% psf: 240-340 |
| 400 μm, 90% psf Tolerances (%) | Tolerance: 30% | Tolerance: 15-30% |
| Magnification Error (%) | 0.04% | 0.04% |
| Overall Length (mm) | 660 mm | 600 mm |

Figure 24:
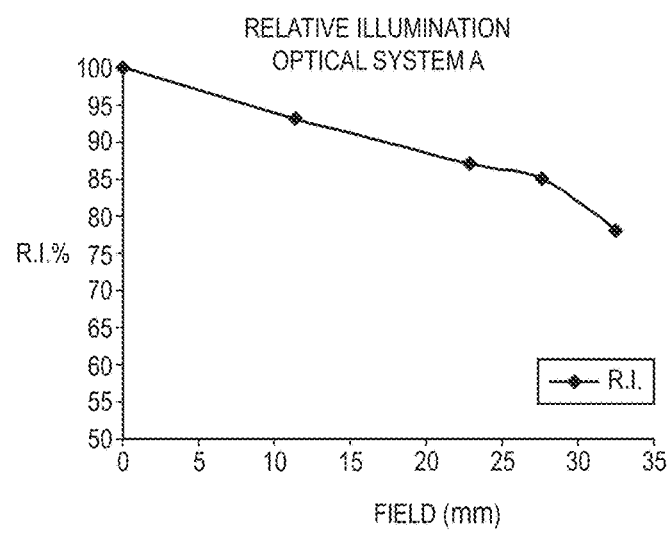
FIG. 24 is a graph of relative illumination in Optical System A for various lateral positions.
Figure 25:
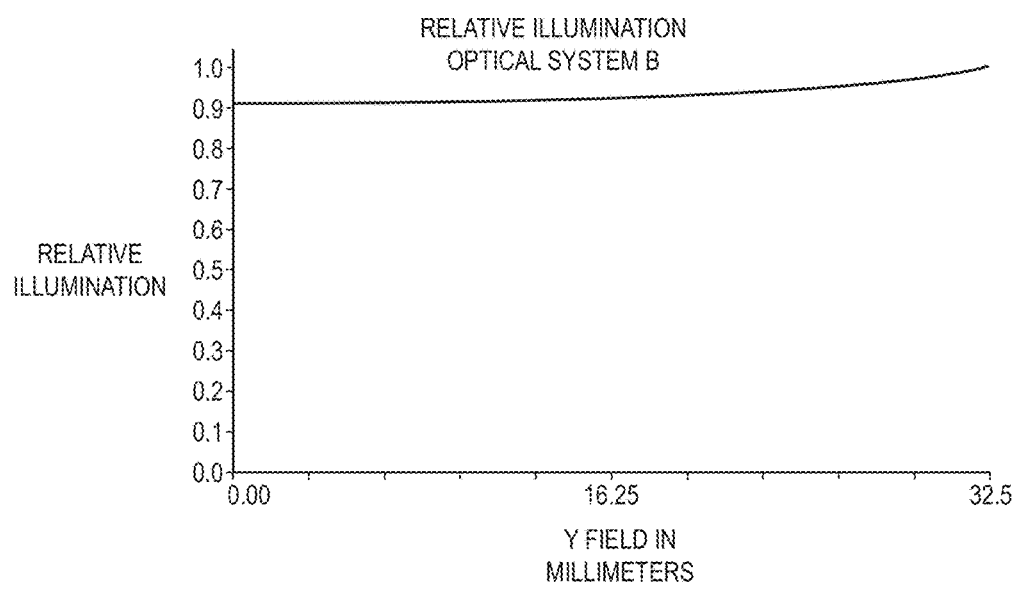
FIG. 25 is a graph of relative illumination in Optical System B for various lateral positions in the source area.

Both Optical System A and Optical System B have good relative illumination. FIG. 24 shows a graph of the relative illumination of Optical System A as a function of lateral displacement. As shown, the relative illumination for Optical System A falls from 100% at the center to about 78% at the edge. FIG. 25 shows a graph of the relative illumination of Optical System B as a function of lateral displacement. As shown, the relative illumination for Optical System B rises from about 92% at the center to 100% at the edge.

Figure 26:
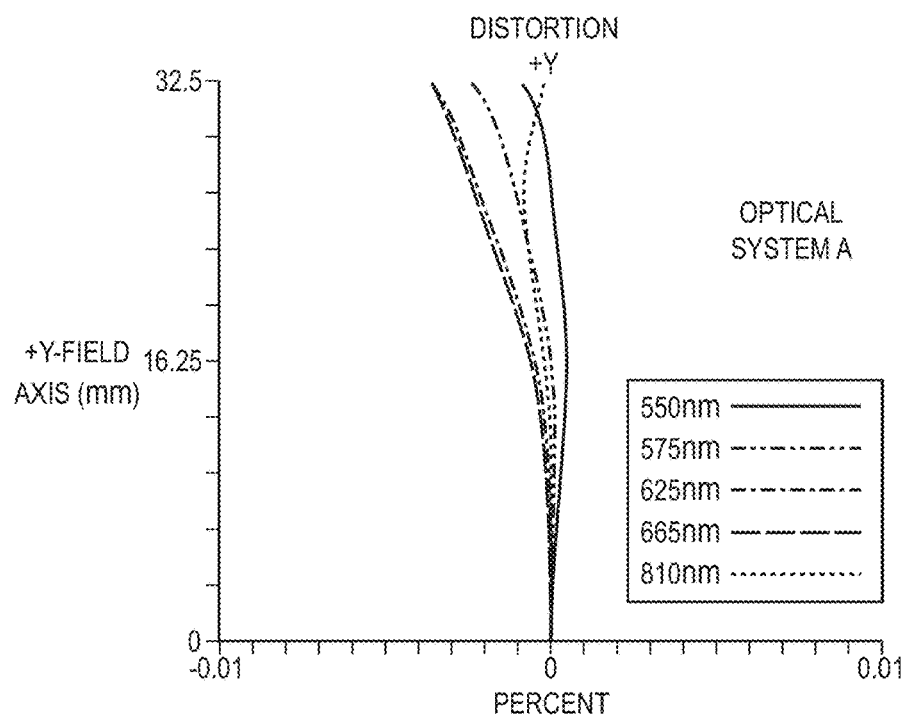
FIG. 26 is a graph of image distortion in Optical System A for various lateral positions.
Figure 27:
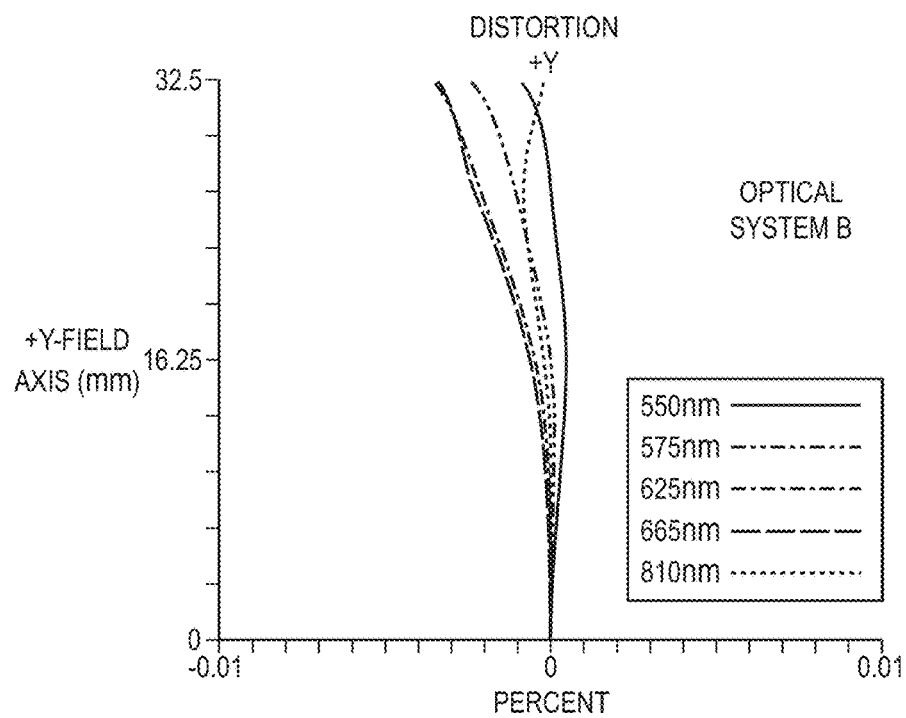
FIG. 27 is a graph of image distortion in Optical System B for various lateral positions.

FIGS. 26 and 27 show the theoretical distortion for Optical System A and Optical System B, respectively, as a function lateral distance. As shown in FIG. 26, the maximum theoretical distortion for Optical System A is about 0.0005%. As shown by FIG. 27, the maximum theoretical distortion for Optical System B is about 0.001%. The actual distortion is limited by the fabrication tolerances of the design.

Figure 28:
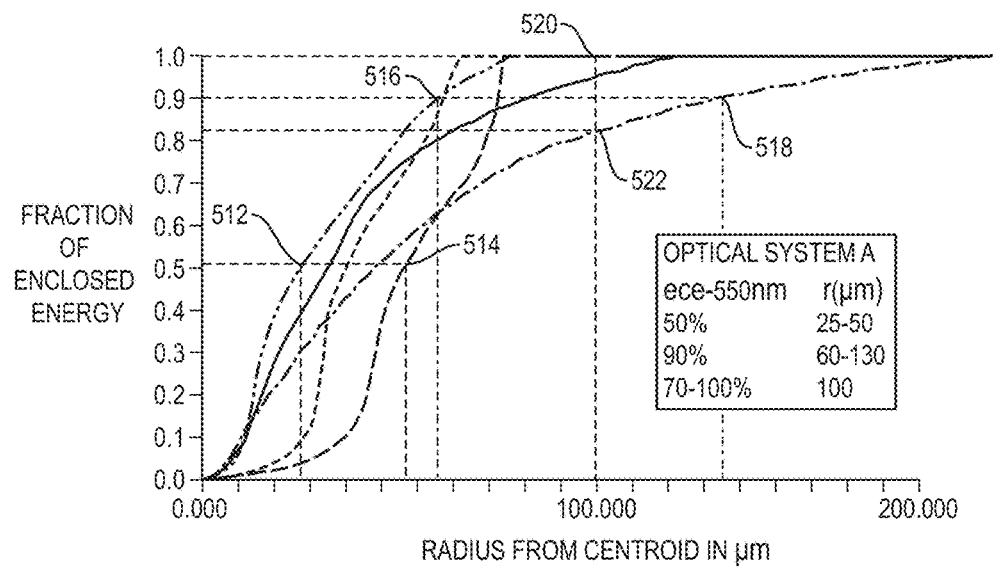
FIG. 28 is a graph of the enclosed energy as a function of radius from the spot center for a 550 nm wavelength point source at different lateral positions for Optical System A.

FIGS. 28-31 are graphs of fraction of encircled (or enclosed) energy (ece) as a function of radius from the centroid for points in the source area having different lateral distances from the central axis. FIG. 28 is a graph of encircled energy for Optical System A for light having a 550 nm wavelength. The graph includes ece as a function of radius for points in the source area offset from the central axis by 0.00 mm, 11.38 mm, 22.75 mm, 27.63 mm, and 32.5 mm. As shown by points 512 and 514, an ece of 50% corresponds to radii falling within a range of about 25-50 μm for point sources with different lateral offsets. As shown by points 516 and 518, an ece of 90% corresponds to radii falling with a range of about 60-130 μm for point sources with different lateral offsets. As shown by points 520 and 522, for a radius of 100 μm, the ece ranges from about 70-100%.

Figure 29:
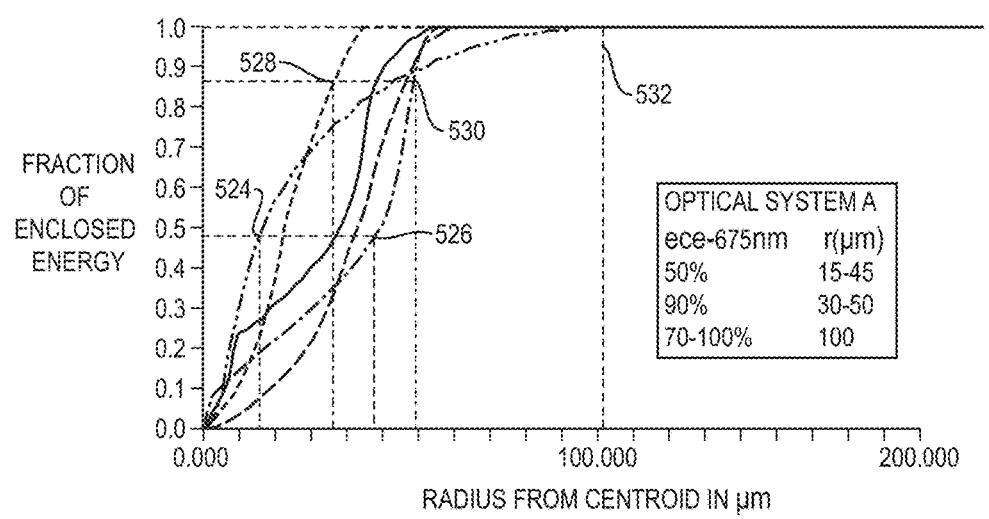
FIG. 29 is a graph of the enclosed energy as a function of radius from the spot center for a 675 nm wavelength point source at different lateral positions for Optical System A.

FIG. 29 is a graph of encircled energy for Optical System A for light having a 675 nm wavelength. The graph includes ece as a function of radius for points sources offset from the central axis by 0.00 mm, 11.38 mm, 22.75 mm, 27.63 mm, and 32.5 mm. As shown by points 524 and 526, an ece of 50% corresponds to radii falling within a range of about 15-45 μm for point sources with different lateral offsets. As shown by points 528 and 530, an ece of 90% corresponds to radii falling with a range of about 30-50 μm for point sources with different lateral offsets. As shown by point 532, for a radius of 100 μm, the ece is about 100% for point sources with various lateral offsets.

Figure 30:
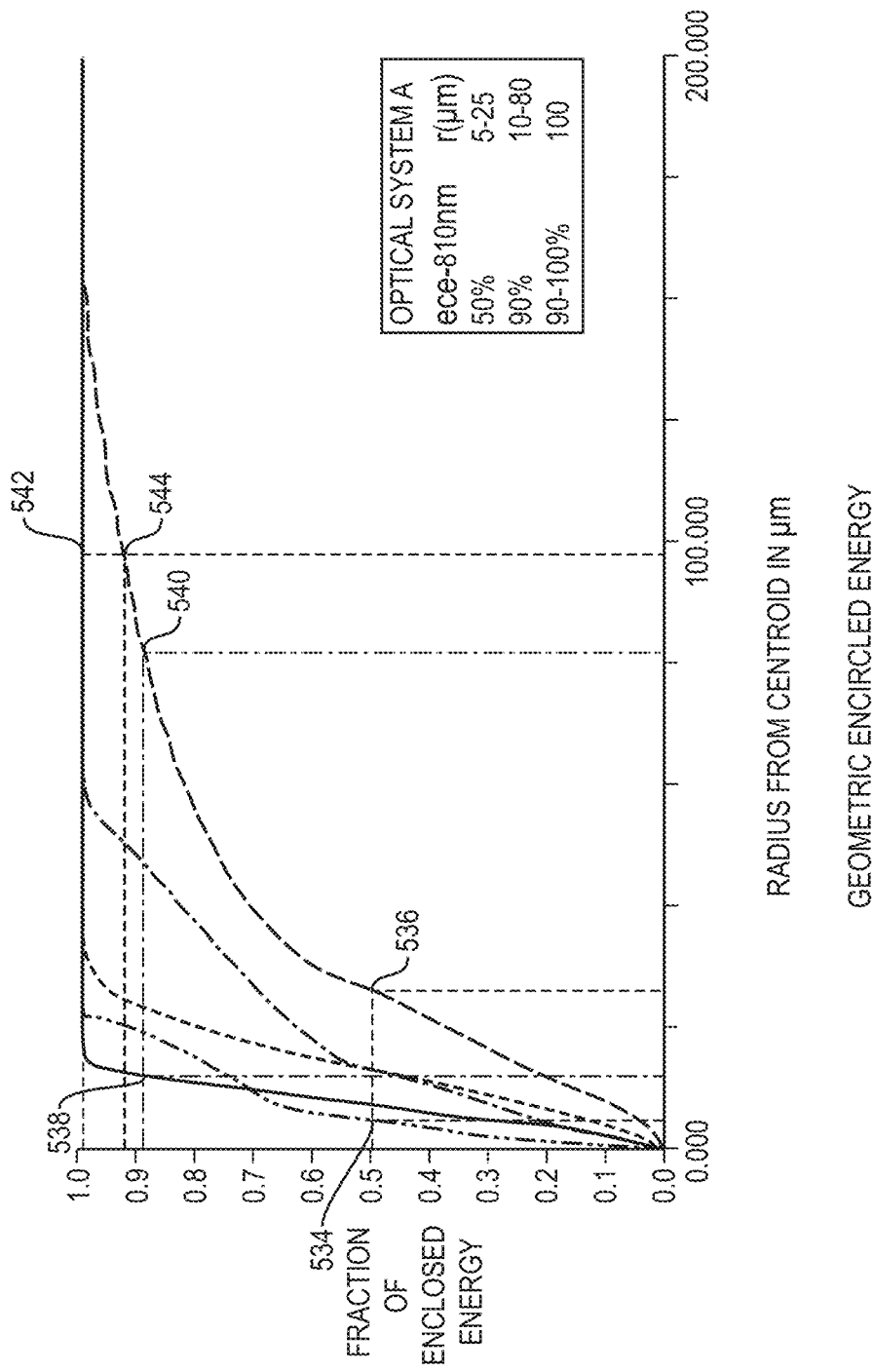
FIG. 30 is a graph of the enclosed energy as a function of radius from the spot center for an 810 nm wavelength point source at different lateral positions for Optical System A.

FIG. 30 is a graph of encircled energy for Optical System A for light having an 810 nm wavelength. The graph includes ece as a function of radius for point sources offset from the central axis by 0.00 mm, 11.38 mm, 22.75 mm, 27.63 mm, and 32.5 mm. As shown by points 534 and 536, an ece of 50% corresponds to radii falling within a range of about 5-25 μm for point sources with different lateral offsets. As shown by points 538 and 540, an ece of 90% corresponds to radii falling with a range of about 10-800 μm for point sources with different lateral offsets. As shown by points 542 and 544, for a radius of 100 µm, the ece falls within a range of about 90-100% for point sources with various lateral offsets.

Figure 31:
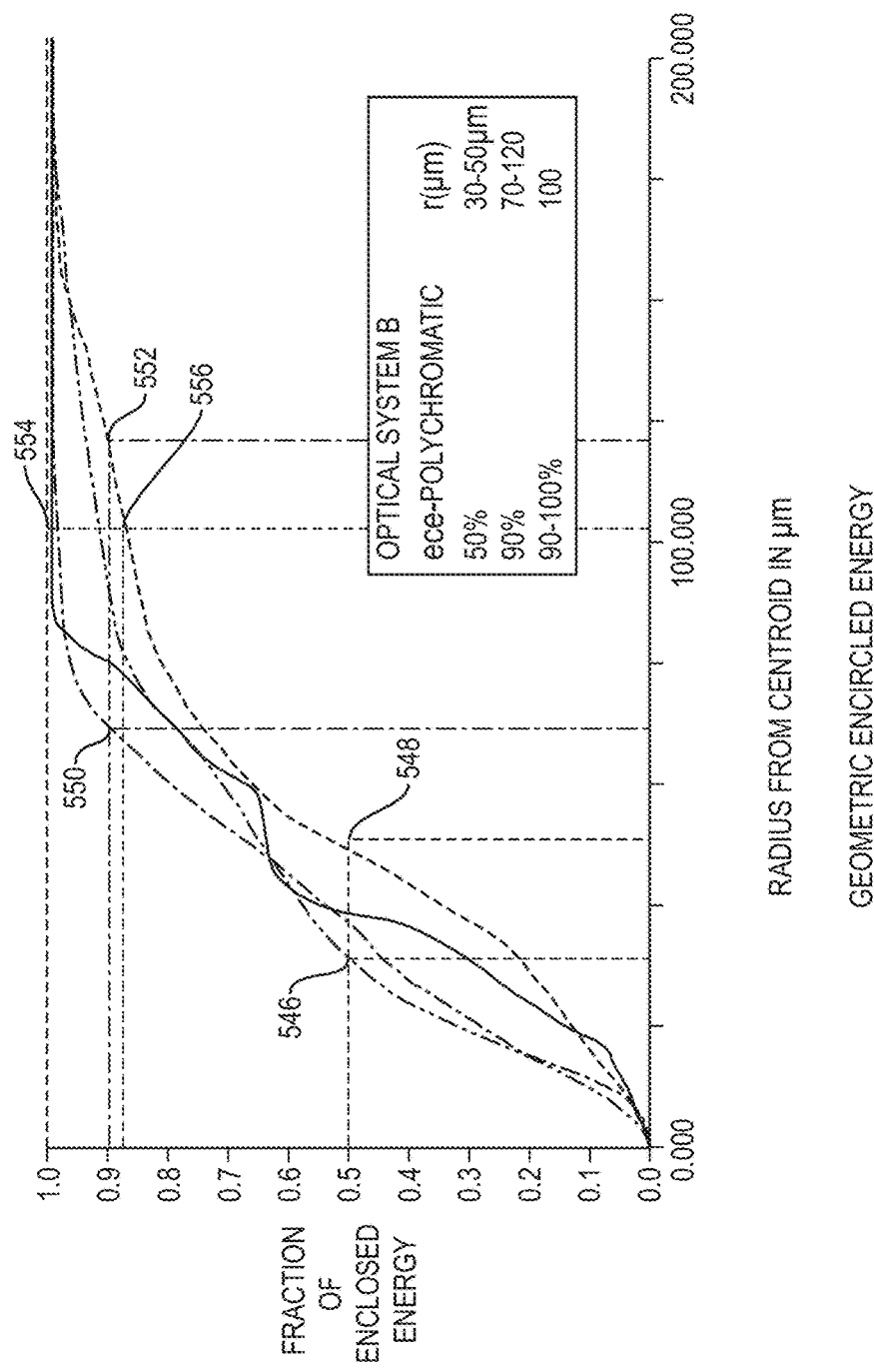
FIG. 31 is a graph of the enclosed energy as a function of radius from the spot center for a polychromatic point source at different lateral positions for Optical System B.

FIG. 31 is a graph of encircled energy for Optical System B for polychromatic light. The graph includes ece as a function of radius from the centroid for point sources offset from the central axis by 0.00 mm, 10.00 mm, 20.00 mm, and 32.50 mm. As shown by points 546 and 548, an ece of 50% corresponds to radii falling within a range of about 30-50 µm for point sources with different lateral offsets. As shown by points 550 and 552, an ece of 90% corresponds to radii falling with a range of about 70-120 µm for point sources with different lateral offsets. As shown by points 554 and 556, for a radius of 100 µm, the ece falls within a range of about 90-100% for point sources with various lateral offsets.

Figure 32:
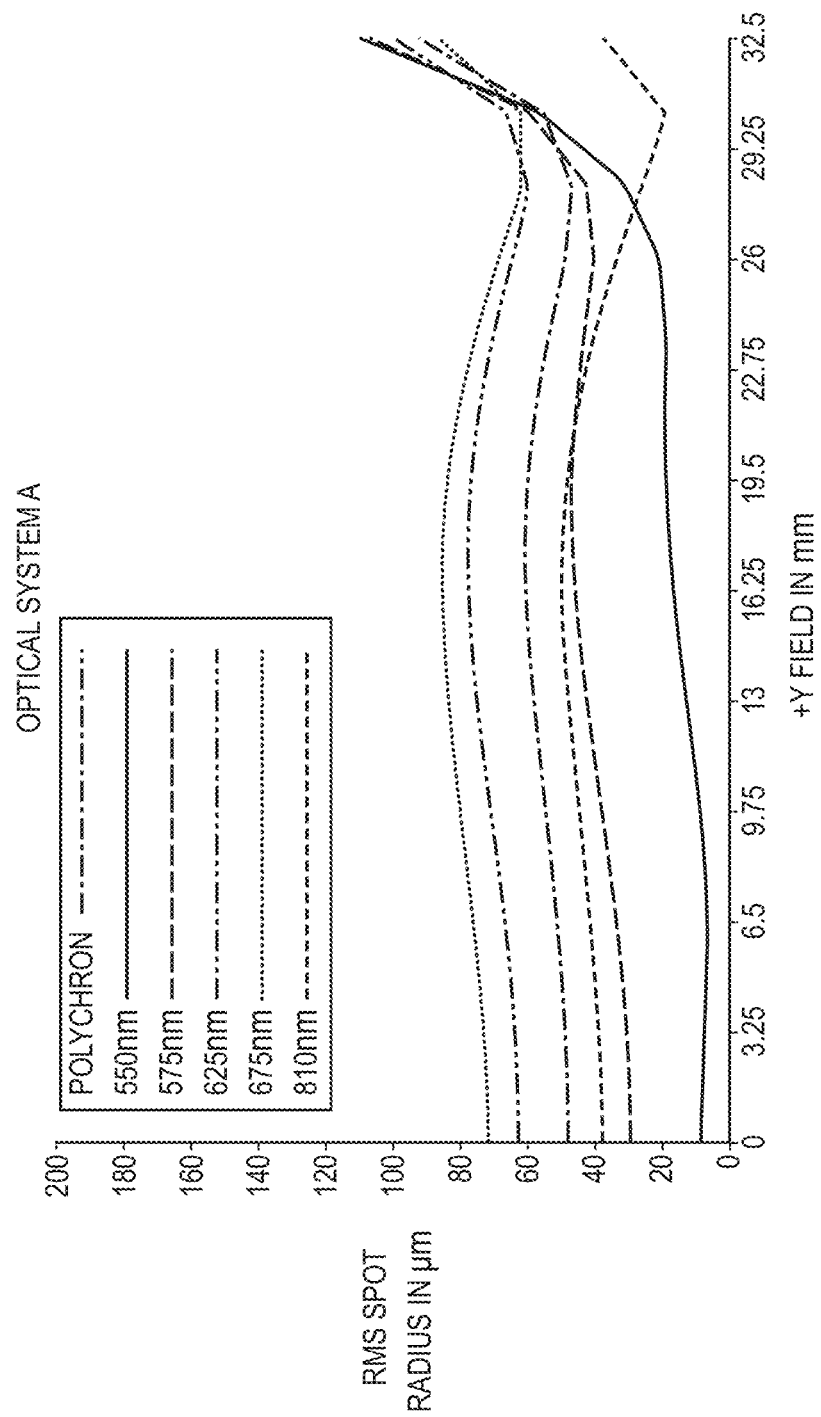
FIG. 32 is a graph of spot radius as a function of lateral position for different wavelengths of light in Optical System A.

FIG. 32 is a graph of RMS spot size for encircling 68% of the energy from a centroid as a function of offset of the centroid from the central axis for Optical System A. The different lines indicate behavior of Optical System A for light of different wavelengths: 550 nm, 575 nm, 625 nm, 675 nm, and 810 nm and polychromatic light.

Figure 33:
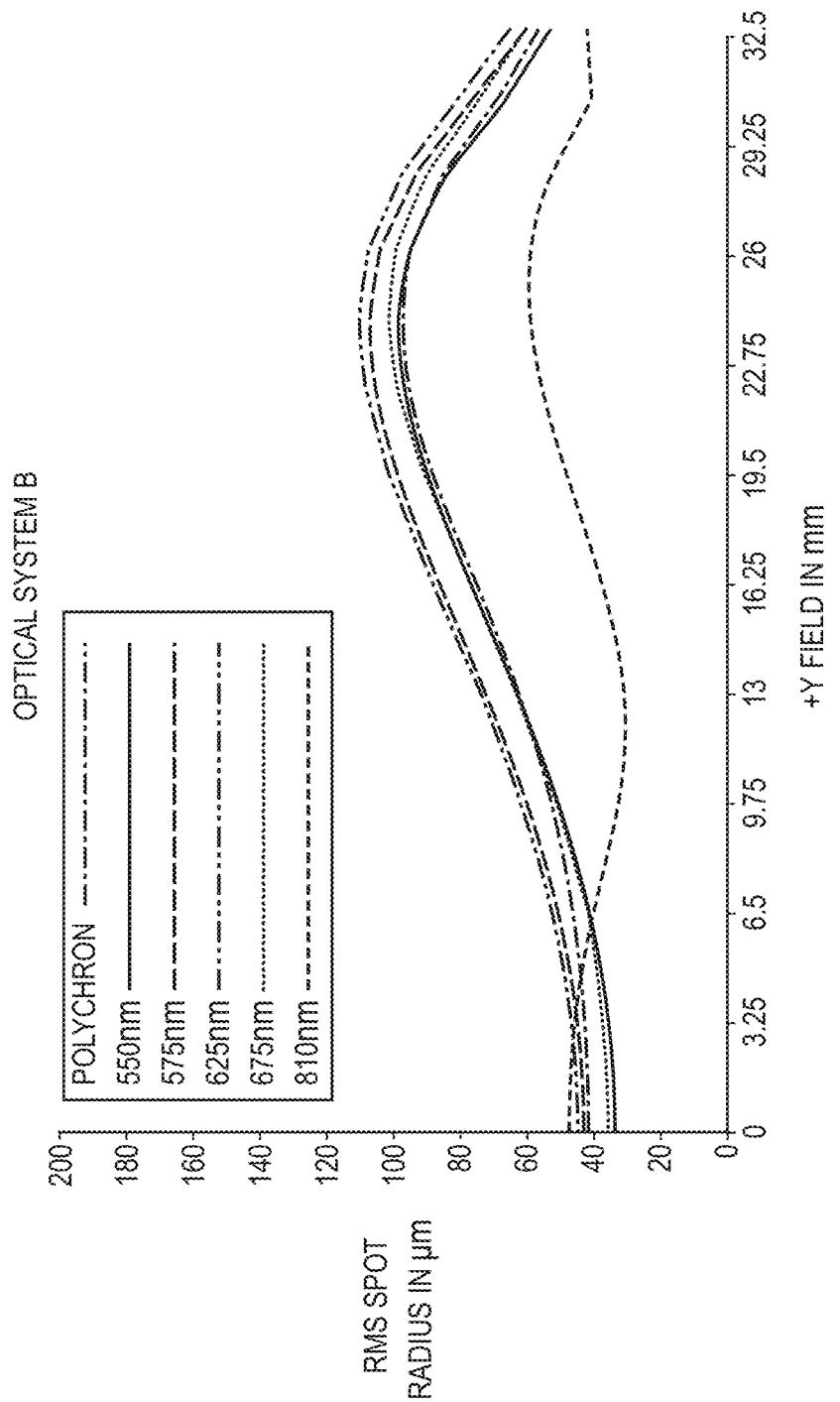
FIG. 33 is a graph of spot radius as a function of lateral position for different wavelengths of light in Optical System B.

FIG. 33 is a graph of RMS spot size for encircling 68% of the energy from a centroid as a function of offset of the centroid from the central axis for Optical System B. The different lines indicate behavior of Optical System B for light of different wavelengths: 550 nm, 575 nm, 625 nm, 675 nm, and 810 nm and polychromatic light.

Figure 34:
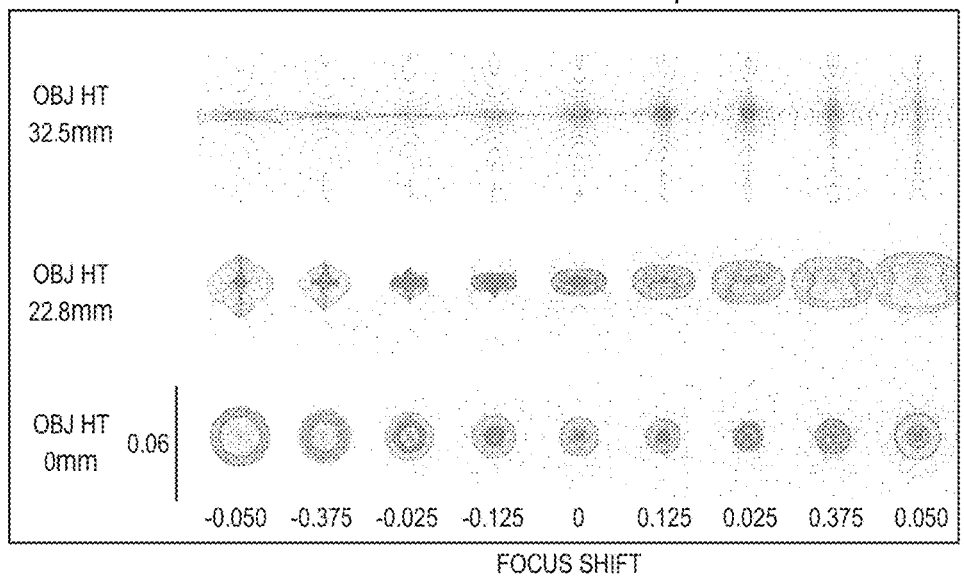
FIG. 34 is a chart of the energy distribution for Optical System A for focal shifts in a range of ±50 µm.
Figure 35:
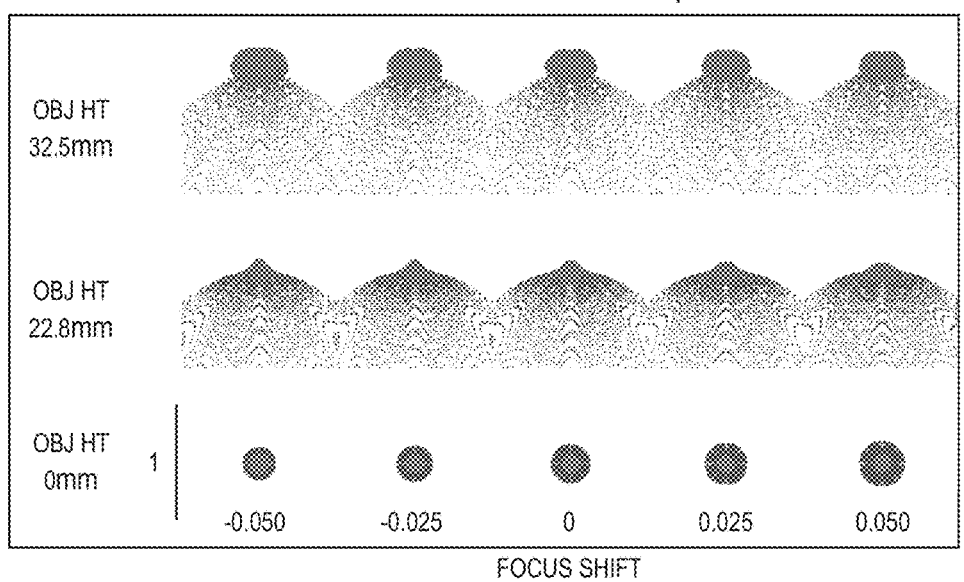
FIG. 35 is a chart of the energy distribution for Optical System B for focal shifts in a range of ±50 µm.

FIGS. 34 and 35 illustrate the focal shift of Optical System A and of Optical System B, respectively, by showing the how the image changes for objects of various heights displaced from the focal plane through a range of +/−50 µm. In FIG. 34, the bottom row of images illustrates the spot sizes at the image plane for a 600 nm wavelength point source positioned at 50 µm, 37.5 µm, 25 µm, and 12.5 µm behind the focal plane, at the focal plane, and at 12.5 µm, 25 µm, 37.5 µm, and 50 µm in front of the focal plane for Optical System A. The middle row of images shows spot sizes for a 22.8 mm tall object at various positions with respect to the focal plane. The top row of images shows spot sizes for a 32.5 mm tall object at various positions with respect to the focal plane.

In FIG. 35, the bottom row of images illustrate the spot size at the image plane for 675 nm and 810 nm wavelength point sources positioned at −50 µm, −25 µm, 0 µm, 25 µm and 50 µm with respect to the focal plane for Optical System B. The middle row of images shows spot sizes for a 22.8 mm tall object at various positions with respect to the focal plane. The top row of images illustrates the spot sizes for at 32.5 mm tall object at various positions with respect to the focal plane.

Figure 36:
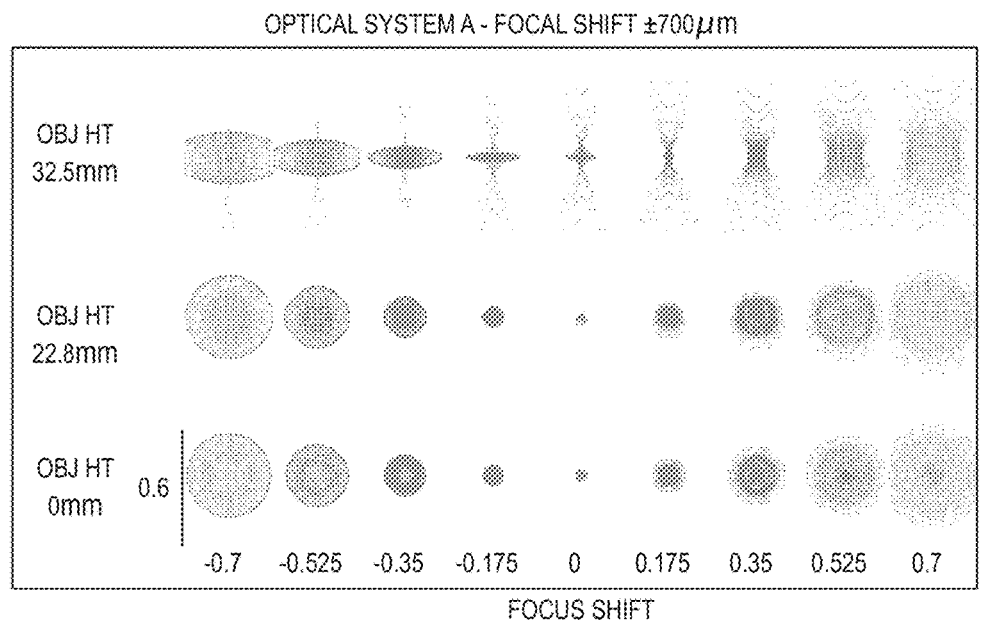
FIG. 36 is a chart of the energy distribution for Optical System A for focal shifts in a range of ±700 µm.
Figure 37:
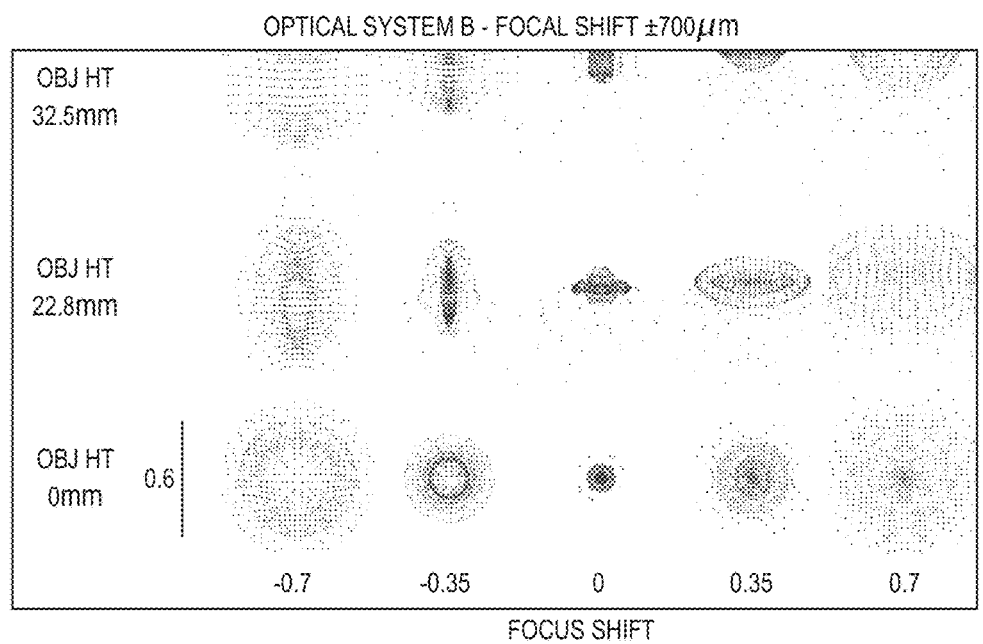
FIG. 37 is a chart of the energy distribution for Optical System B for focal shifts in a range of ±700 µm.

FIGS. 36 and 37 illustrate the focal shift of Optical System A and of Optical System B, respectively, by showing the how the image changes when objects of various heights are displaced from the focal plane through a range of +/−700 µm. In FIG. 36, the bottom row of images illustrates the spot sizes at the image plane for a 600 nm wavelength point source positioned at 700 µm, 525 µm, 350 µm and 175 µm behind the focal plane, at the focal plane, and at 175 µm, 350 µm, 525 µm and 700 µm in front of the focal plane for Optical System A. The middle row of images show spot sizes for a 22.8 mm tall object positioned at −700 µm, −525 µm, −35 0µm, 175 µm, 0 µm, 17 5 µm, 350 µm, 525 µm and 700 µm with respect to the focal plane. The top row of images shows spot sizes for a 32.5 mm tall object at various positions with respect to the focal plane.

In FIG. 37, the bottom row of images illustrate the spot sizes at the image plane for 675 nm and 810 nm wavelength point sources positioned at −700 µm, −350 µm, 0 µm, 350 µm and 700 µm with respect to the focal plane. The middle row of images shows spot sizes for a 22.8 mm tall object at various positions with respect to the focal plane. The top row of images illustrates the spot sizes for at 32.5 mm tall object at various positions with respect to the focal plane.

The present invention has been described relative to illustrative embodiments. Because certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall there between.

The invention claimed is:

1. A large area, low f-number optical system for collecting light from a plurality of micro channels associated with a plurality of flow cytometers, the optical system comprising:
    a plurality of optical elements disposed along an optical path of the system; and
    a mounting system for mounting the plurality of optical elements along the optical path, the plurality of optical elements configured to:
        simultaneously collect light across the plurality of micro channels distributed over a source area having a length or width within a range of 10 mm to 75 mm; and
        have a working distance between the source area and a first optical element in the plurality of optical elements along the optical path within a range of 10 mm to 30 mm.

2. The optical system of claim 1, wherein the plurality of optical elements comprises a plurality of non-aspheric lenses.

3. The optical system of claim 1, wherein the optical system has one to one magnification.

4. The optical system of claim 1, wherein a magnification of the optical system is within a range of 0.5 to 5.

5. The optical system of claim 1, wherein the plurality of optical elements comprises an optical filter disposed in the optical path.

6. The optical system of claim 1, further comprising an array of input apertures disposed in proximity to the source area.

7. The optical system of claim 1, further comprising an array of output apertures disposed in proximity to an image plane.

8. The optical system of claim 1, further comprising an array of apertures positioned to filter in a Fourier transform plane.

9. The optical system of claim 1, wherein the plurality of optical elements comprises a first set of optical elements that collects and collimates light and a second set of optical elements that focuses the collimated light.

10. The optical system of claim 9, wherein the first set of optical elements comprises a first set of lenses, and wherein the second set of optical elements comprises a second set of lenses.

11. The optical system of claim 10, wherein the first set of lenses and the second set of lenses form an air-spaced achromatic lens pair.

12. The optical system of claim 10, wherein the first set of lenses comprises seven or more substantially co-axial lenses and the second set of lenses comprises seven or more substantially co-axial lenses.

13. The optical system of claim 1, wherein the plurality of flow cytometers is associated with a multi-channel sorter.

14. A multi-channel microfluidic system comprising:
a receptacle for receiving a multi-channel microfluidic chip having a plurality of microfluidic channels;
one or more light sources for illuminating at least a portion of each microfluidic channel in the plurality of microfluidic channels;
an optical system for collecting light from the plurality of microfluidic channels, the optical system comprising:
a plurality of optical elements disposed along an optical path of the system; and
a mounting system for mounting the plurality of optical elements along the optical path, the plurality of optical elements configured to:
simultaneously collect light from the plurality of microfluidic channels distributed over a source area having a length or width within a range of 10 mm to 75 mm; and
have a working distance between the source area and a first optical element in the plurality of optical elements along the optical path within a range of 10 mm to 30 mm; and
one or more detectors for detecting light output from the optical system.

15. The multi-channel microfluidic system of claim 14, wherein the microfluidic channels are associated with a plurality of flow cytometers.

16. The multi-channel microfluidic system of claim 14, wherein the microfluidic system is a particle sorting system that sorts particles in the plurality of microfluidic channels.

17. The multi-channel microfluidic system of claim 14, further comprising a plurality of optical fibers for receiving light from the optical system and transmitting the light to the one or more detectors.

18. The multi-channel microfluidic system of claim 17, wherein each optical fiber receives light from one microfluidic channel.

19. The multi-channel microfluidic system of claim 14, wherein the one or more light sources simultaneously illuminates at least a portion of each micro-fluidic channel.

20. The multi-channel microfluidic system of claim 14, wherein the optical system comprises a long pass filter having an optical density profile selected to attenuate a magnitude of an incident scattered light signal from at least one of the one or more light sources to be comparable to a magnitude of an expected incident fluorescent signal.

21. A method of detecting scattered and/or emitted light by a liquid and/or a particle in a microfluidic system, the method comprising:
illuminating the liquid and/or particle with at least one light source;
receiving a first light having a first wavelength and a second light having a second wavelength using an optical system having a primary optical path;
attenuating the first light such that a magnitude of the attenuated first light is comparable to a magnitude of the second light in the primary optical path; and
detecting the attenuated first light and the second light using one or more detectors in the primary optical path.

22. The method of claim 21, wherein the first light is a scattered source light and the second light is an emitted fluorescent light.

23. The method of claim 21, wherein the optical system has an optical filter in the primary optical path, and wherein the step of attenuating includes attenuating the first light using the optical filter.

24. The method of claim 21, wherein the optical system has a leaky filter in the primary optical path, and wherein the step of attenuating includes attenuating the first light using the leaky filter.

25. The method of claim 21, wherein the step of detecting includes using a single detector.

\* \* \* \* \*